(12) United States Patent
Lowe et al.

(10) Patent No.: US 10,376,881 B2
(45) Date of Patent: Aug. 13, 2019

(54) ASSAY DEVICE AND READER

(75) Inventors: Phillip Lowe, Clarkmananshire (GB);
Steven Alexander Keatch, Stirling (GB); Brian McGuigan, Stirling (GB)

(73) Assignee: LumiraDx UK Ltd., London (GB)

( * ) Notice: Subject to any disclaimer, the term of this patent is extended or adjusted under 35 U.S.C. 154(b) by 648 days.

(21) Appl. No.: 13/820,928

(22) PCT Filed: Sep. 7, 2011

(86) PCT No.: PCT/GB2011/001315
§ 371 (c)(1),
(2), (4) Date: May 20, 2013

(87) PCT Pub. No.: WO2012/032294
PCT Pub. Date: Mar. 15, 2012

(65) Prior Publication Data
US 2013/0309778 A1    Nov. 21, 2013

(30) Foreign Application Priority Data

Sep. 7, 2010    (GB) .................................. 1014805.4

(51) Int. Cl.
*B01L 3/00* (2006.01)
*G01N 33/543* (2006.01)
(Continued)

(52) U.S. Cl.
CPC ......... *B01L 3/502715* (2013.01); *B01L 3/527* (2013.01); *G01N 33/54326* (2013.01);
(Continued)

(58) Field of Classification Search
CPC ...... B01L 3/502715; B01L 3/527; B01L 7/00;
B01L 2200/027; B01L 2200/0668; B01L
2200/0684; B01L 2200/10; B01L
2300/0609; B01L 2300/0645; B01L
2300/0654; B01L 2300/0816;
(Continued)

(56) References Cited

U.S. PATENT DOCUMENTS 4,806,313 A   2/1989 Ebersole et al.
5,096,669 A   3/1992 Lauks et al.
(Continued)

FOREIGN PATENT DOCUMENTS

JP   2004-301767 A   10/2004
JP   2007-333706 A   12/2007
(Continued)

OTHER PUBLICATIONS

PCT Search Report and Written Opinion for PCT/GB2011/001315, completed Dec. 13, 2012.
(Continued)

*Primary Examiner* — Melanie Brown
(74) *Attorney, Agent, or Firm* — Goodwin Procter LLP

(57) ABSTRACT

The present invention relates to a microfluidic based assay system, comprising a disposable assay cartridge and associated reading device, as well as the individual components themselves. The present invention also relates to methods of conducting assays, using the cartridge and device of the invention, as well as kits for conducting assays.

12 Claims, 23 Drawing Sheets

(51) Int. Cl.
*G01N 35/00* (2006.01)
*B01L 7/00* (2006.01)

(52) U.S. Cl.
CPC ... *G01N 33/54386* (2013.01); *G01N 35/0098* (2013.01); *B01L 7/00* (2013.01); *B01L 2200/027* (2013.01); *B01L 2200/0668* (2013.01); *B01L 2200/0684* (2013.01); *B01L 2200/10* (2013.01); *B01L 2300/0609* (2013.01); *B01L 2300/0645* (2013.01); *B01L 2300/0654* (2013.01); *B01L 2300/0816* (2013.01); *B01L 2400/043* (2013.01); *B01L 2400/0487* (2013.01); *B01L 2400/0688* (2013.01)

(58) Field of Classification Search
CPC ....... B01L 2400/043; B01L 2400/0487; B01L 2400/0688; G01N 3/502715; G01N 3/527; G01N 7/00; G01N 2200/027; G01N 2200/0668; G01N 2200/0684; G01N 2200/10; G01N 2300/0609; G01N 2300/0645; G01N 2300/0654; G01N 2300/0816; G01N 2400/043; G01N 2400/0487; G01N 2400/0688; G01N 35/0098; G01N 33/54386; G01N 33/54326
USPC ........................................................ 436/526
See application file for complete search history.

(56) References Cited

U.S. PATENT DOCUMENTS

| | | | |
|---|---|---|---|
| 5,842,787 A | 12/1998 | Kopf-Sill et al. | |
| 5,866,345 A | 2/1999 | Wilding et al. | |
| 5,932,100 A | 8/1999 | Yager et al. | |
| 5,957,579 A | 9/1999 | Kopf-Sill et al. | |
| 6,982,146 B1* | 1/2006 | Schneider | C12Q 1/6869 435/6.12 |
| 8,512,648 B2 | 8/2013 | Bau-Madsen | |
| 9,233,370 B2 | 1/2016 | Miller et al. | |
| 9,341,620 B2 | 5/2016 | Lowe et al. | |
| 2003/0040129 A1* | 2/2003 | Shah | B01L 3/5027 506/32 |
| 2003/0170881 A1 | 9/2003 | Davis et al. | |
| 2004/0086427 A1 | 5/2004 | Childers et al. | |
| 2004/0151629 A1* | 8/2004 | Pease | B01L 3/5027 422/68.1 |
| 2004/0189311 A1* | 9/2004 | Glezer | B01L 3/5027 324/444 |
| 2005/0030033 A1 | 2/2005 | Peck et al. | |
| 2005/0041525 A1 | 2/2005 | Pugia et al. | |
| 2005/0054078 A1 | 3/2005 | Miller et al. | |
| 2006/0257958 A1 | 11/2006 | Bruno | |
| 2007/0031283 A1* | 2/2007 | Davis et al. | 422/58 |
| 2007/0037225 A1 | 2/2007 | Metzger et al. | |
| 2008/0025872 A1 | 1/2008 | Dykes et al. | |
| 2008/0318798 A1 | 12/2008 | Campbell et al. | |
| 2009/0130658 A1 | 5/2009 | Barlag et al. | |
| 2009/0263891 A1 | 10/2009 | Gillies et al. | |
| 2009/0298059 A1 | 12/2009 | Gumbrecht et al. | |
| 2010/0009431 A1 | 1/2010 | Cho et al. | |
| 2010/0075311 A1 | 3/2010 | Barrault et al. | |
| 2011/0067489 A1* | 3/2011 | Haberstroh | B01L 3/50857 73/64.56 |
| 2012/0031773 A1* | 2/2012 | Miller | B01L 3/502761 205/777.5 |
| 2012/0071342 A1 | 3/2012 | Lochhead et al. | |
| 2012/0270225 A1 | 10/2012 | Wakeley et al. | |
| 2013/0224775 A1 | 8/2013 | Davis et al. | |
| 2014/0212882 A1 | 7/2014 | Handique et al. | |
| 2015/0024426 A1 | 1/2015 | De Oliveira Garcia Da Fonseca et al. | |
| 2015/0087079 A1 | 3/2015 | Coffey et al. | |
| 2016/0320374 A1 | 11/2016 | Lowe et al. | |

FOREIGN PATENT DOCUMENTS

| | | |
|---|---|---|
| JP | 2010-117308 A | 5/2010 |
| WO | WO-2004/011925 A1 | 2/2004 |
| WO | WO-2005/030033 A2 | 4/2005 |
| WO | WO-2006/022495 A1 | 3/2006 |
| WO | WO2007089753 | 8/2007 |
| WO | WO-2009/108260 A2 | 9/2009 |
| WO | WO2009115608 | 9/2009 |
| WO | WO-2011/123064 A1 | 10/2011 |
| WO | WO-2013/096801 A1 | 6/2013 |

OTHER PUBLICATIONS

Wang et al. (2007) "Microsystem design and production," p. 597-602 with English translation of p. 599, paragraph 2 (8 pages).

Liu, H.-B. et al. (2012) "Manipulating liquid plugs in microchannel with controllable air vent," Biomicrofluidics, 6: 012815.

"Electrochemical Sensors, Biosensors and Their Biomedical Applications," Edited by Xueji Zhang et al. (2008), Chapter 11 "Biochips—fundamentals and applications" (100 pages).

International Search Report and Written Opinion for International Patent Application No. PCT/GB2017/051946, dated Dec. 6, 2017 (33 pages).

* cited by examiner

Valve System: 1 input, 4 outputs, each of the 4 outputs is split as there are 2 channels (so 2 sets of 4 inlets)

6 wash ports connected directly from wash cartridge to meter – strip fluidic interface 6 chamber syringe cartridge

ASSAY DEVICE AND READER

CROSS-REFERENCE TO RELATED APPLICATIONS

This application is a national stage entry under 35 U.S.C. § 371(b) of International Application No. PCT/GB2011/001315, filed Sep. 7, 2011, which claims the benefit of United Kingdom Patent Application Serial No. 1014805.4, filed Sep. 7, 2010, the disclosures of both which are herein incorporated by reference.

FIELD OF THE INVENTION

The present invention relates to a microfluidic based assay system, comprising a disposable assay cartridge and associated reading device, as well as the individual components themselves. The present invention also relates to methods of conducting assays, using the cartridge and device of the invention, as well as kits for conducting assays.

BACKGROUND TO THE INVENTION

The in vitro diagnostics (IVD) market is highly competitive and there is a constant need within the IVD market to develop fast, low volume, precise and cheap IVD tests. This is coupled with the fact there is a strong market desire to develop capillary finger stick blood tests with reduced user complexity to allow total market penetration (e.g. point of care, doctors surgery, home etc). This capillary finger stick IVD testing model has proved hugely successful for diabetes testing developing into a $3.5 billion market (ref: Medical Device Today). The desire and ability to evolve immunoassay IVD towards capillary finger stick blood testing has been hampered by technology developments, however this remains a golden aim of many diagnostic companies as it allows reduced complexity and greater placement of products in existing or untapped market.

It is amongst the objects of the present invention to provide a cheap and reliable assay system for carrying out IVD tests.

It is amongst the objects of the present invention to provide an assay cartridge design platform and reader which may be easily and cheaply fabricated, as well as being able to be configured to carry out a specified assay or assays.

It is amongst the objects of the present invention to provide an assay cartridge which may easily be adapted to carry out a variety of different specified assays.

It is amongst the objects of the present invention to provide an assay system comprising a reader which may preferably be used or easily adapted to perform a variety of different assays.

SUMMARY OF THE INVENTION

In a first aspect the present invention provides a microfluidic assay cartridge for use in detecting an analyte in a sample of fluid, the cartridge comprising:

a substrate comprising one or more microfluidic channels disposed therein and comprising a binding agent disposed within said channel(s) for binding any of said analyte within the sample;

a sample port for introducing said fluid sample into the cartridge;

at least one fluid input port for allowing one or more fluids to be introduced to the cartridge from an associated reader device and transported through the microfluidic channel(s); and a fluid outlet sink for removing fluid from said channel(s).

The cartridge may further comprise a detection area where any bound analyte may be detected. The detection area maybe be contained within the sample channel, which is directly adjacent or downstream from the sample port.

The cartridge design of the present invention may easily be adapted to carry out a number of different assays and hence can be considered as an assay platform for a variety of assays. The cartridge and channel(s) disposed therein may be formed in any manner of ways known to the skilled addresses, which may include photolithography, wet chemical etching, laser ablation, injection moulding, embossing and printing techniques. However, in a preferred embodiment, the cartridge and the channels and other features disposed therein, are formed by a sandwich of three separate substrates—a top, middle and bottom substrate.

The cartridge can be formed of any suitable material, such as polycarbonate, polyester, polystyrene, PMMA, etc. and the/each substrate may be formed of a single or plurality of material(s). In the embodiment comprising three substrates, the middle substrate comprises a pattern cut through the substrate, corresponding to certain features of the cartridge, such as the channel(s), fluid reservoir/reservoirs port, sink area and the like. By applying and sandwiching (such as by heat sealing, gluing, stapling and the like) appropriately cut top and bottom substrates, to sandwich the middle substrate between the top and bottom substrates, a cartridge can be provided in which channels and other features are disposed. Openings or features in the top and/or bottom substrate may be designed to co-locate with features in a reader device (as will be discussed hereinafter), which may facilitate with correct location of the cartridge in the reader and also importantly allow for a fluid, such as a wash buffer, to be introduced from a fluid reservoir/reservoirs in the reader to the cartridge or sample to be applied or air to be vented from the cartridge. The fluid/wash buffer or gas can be introduced into the cartridge by way of suitable means such as a pump/pumps means in the reader and the fluid transport means can therefore control fluid transport within the cartridge itself. Thus once a sample has been introduced into the cartridge such as by way of capillary action, further fluid transport within and throughout the cartridge is controlled/facilitated by way of means provided in the reader device. It will be appreciated that the fluid introduced into the cartridge by way of the fluid input port may be a liquid and/or a gas, such as air.

As identified, in use, the sample is applied to the cartridge through a sample introduction port such as by way of capillary action or other means. In a preferred embodiment the sample introduction port is an aperture in a side or face of the cartridge. Desirably the cartridge is in the form of a generally thin planar device comprising top and bottom faces and four edges. In this arrangement, the sample introduction port may be formed in one of the edges of the cartridge, so that a user need only contact the sample with the aperture formed in the edge, in order to enable sample uptake into the cartridge. In use the user contacts the fluid sample with the port/aperture and, in certain embodiments, due to the dimensions of said channel(s) within the cartridge, fluid is drawn into the cartridge by capillary action. The dimensions of the sample port/aperture may be smaller than the dimensions of the channel(s).

When fluid is being transported through the cartridge, fluid is not expelled through the sample port as there are no surfaces to wet. However, because the sink offers a large void area which can be wetted the preferential fluidic path is into the sink.

Said fluid input port(s) of the cartridge is/are adapted to co-locate with a feature in the reader, so that a fluid, such as a wash buffer or gas, such as air, contained in a reservoir/reservoirs within the reader, can be introduced into the cartridge. Typically the inlet port is simply an aperture or hole within the top surface of the cartridge. The cartridge may include more than one input port, so that a fluid, or fluids, may be added at different time points and/or locations within the cartridge. It is to be understood that a fluid-tight seal is generally formed between each said input port of the cartridge and a feature, such as a valve or tubing within the reader, which may be connected to the reservoir fluid.

Desirably, said channel(s) in the cartridge also comprise one or more fluid stop features, which are designed to prevent the sample and/or other fluids from passing through the stop feature, by virtue of capillary action alone. That is, the sample or any other fluid may be actively forced past said stop feature(s) by a force, such as that applied by a pump/pumps provided by the reader. A preferred stop feature is a hydrophobic material (e.g. printable conductive or non conductive inks) or a process or material that changes the surface properties of a channel surface therefore creating a hydrophilic/hydrophobic differential (e.g. by way of laser ablation, surface scoring, surface material removal, evaporated metallic materials etc), which is designed to abut/be a wall feature or is coated on a wall of the channel. In the embodiment where the channels are formed by virtue of three substrates being sandwiched together thereby forming the channels, the hydrophobic material may be applied to the top and/or bottom substrates, such that when the three substrates are sandwiched together, the hydrophobic stop material forms a feature on the top and/or bottom surface of said channel.

It is also preferred that a stop feature be located upstream of the sink feature, in order that the sample, upon initial application, does not flow into the sink feature. Only when a force, such as provided by way of a pump/pumps, within the reader is applied, can fluid pass the stop feature upstream of the sink feature and hence allow fluid to pass into the sink. The fluid outlet sink is designed to be a void area of the cartridge into which spent fluid or fluid which is not required or deemed undesirable, may be evacuated. For example, whole blood contains many proteins and other agents which can interfere with assay reactions and/or detection of captured analyte, by way of fluorescence detection, for example. The present invention allows the initial binding of any analyte to be carried out within the sample of whole blood, but all or substantially all of the unbound material can subsequently be evacuated to the sink feature, enabling further reactions and/or detection to be carried out in a defined media or buffer.

As well as the microfluidic channel(s), the cartridge of the present invention may comprise one or more electrode features which contact with the channel and hence the sample once introduced into the cartridge. The electrodes are designed to contact electrical contacts within the reader, enabling a variety of readings to be taken, where appropriate. For example, one or more electrodes in the cartridge may be designed to detect correct loading of the cartridge and the reader may signal to the user whether or not the cartridge has a) been correctly inserted into the reader and/or the sample loaded into the cartridge correctly. The electrode(s) may also carry out one or more electrical measurements on the sample itself. For example, when the sample is a sample of whole blood, the electrode(s) may conduct a hematocrit measurement of the sample, which may be important in determining an accurate concentration of the analyte to be detected. Conductivity and/or impedance measurements may be determined depending on the sample being studied. Thus, the cartridges of the present invention may not only detect whether or not an analyte is present in a sample by way of binding any analyte, but electrical measurements on the sample may also be conducted.

The sample to be applied to the cartridge may be any suitable fluid sample. It may for example be a sample of fluid obtained from a subject, such as a whole blood, plasma, saliva, semen, sweat, serum, menses, amniotic fluid, tears, a tissue swab, urine, cerebrospinal fluid, mucous and the like. It is to be appreciated that the assay systems of the present invention may be applied in the human health area, including large and growing IVD markets (e.g. cancer, cardiology, and infectious disease). The assays may also be used to test drugs and drug action. However, the system may also be applied in environmental settings where it is desirable to detect, for example toxic agents or infectious agents such as bacteria or viruses. Thus, samples from rivers or lakes or swabs from solid surfaces may be taken in order to obtain a fluid sample for providing to the cartridge. The assay systems may also be utilised for veterinary applications. Essentially any assay in which a sample can be provided in a fluid form may be utilised in the present invention.

The sample may, for instance, include materials obtained directly from a source, such as a sample of whole blood, as well as materials pretreated using techniques, such as filtration, precipitation, dilution, distillation, mixing, concentration, inactivation of interfering agents, etc. These steps may be carried out prior to the sample being introduced to the cartridge or may be carried out by the cartridge itself.

The sample may be introduced prior to the cartridge being inserted into the reader or after the cartridge has been inserted into the reader. The cartridge may be so designed that the sample is introduced by way of capillary action, or by virtue of a seal being formed between an input port of the cartridge and the reader, the sample may be actively drawn into the cartridge by way of air being drawn through the microfluidic channel(s) by a pump/pumps in the reader, such as a pump/pumps.

The analyte to be detected can be any desired analyte and may include proteins, peptides, antibodies, nucleic acid, microorganisms (such as bacteria and viruses), chemical agents, toxins, pharmaceuticals, metabolites, cellular moieties and the like. For example, the present system may be adapted to detect any type of analyte that can bind a suitable binding agent. The binding agent may be any suitable agent which is able to bind specifically to the analyte to be detected. For example, if the analyte is a protein or peptide, the binding agent may be a receptor or antibody which is capable of specifically binding to the protein/peptide. Conversely an antibody may be bound by a protein/peptide which the antibody is designed to specifically bind to. Nucleic acids may be bound by other nucleic acids which are capable of specifically hybridising to the analyte nucleic acid. Microorganisms may be bound by antibodies which specifically bind to proteins on the surface of the microorganism. Chemical agents, toxins, pharmaceuticals, metabolites may be bound by chemical moieties which are capable or reacting or binding to the aforementioned chemical analytes via appropriate bonding reactions, or affinities. Many types of binding techniques are well known to those of skill in the art.

Moreover, the binding agent may be an enzyme or an enzyme substrate. For example analytes such as glucose through well described enzymatic methodologies may be deleted, for example the reaction product formed following the enzyme reacting with the glucose may be detected by using electrochemical, or optical detection techniques known to the skilled addressee. Such measurements can be made as standalone measurements or in combination with other analytes to be detected in the sample.

The binding agent may itself by attached directly to a wall or surface of said channel within the cartridge, by suitable bonding to the wall or surface for example, by way of physical adsorption, covalent chemical coupling, non covalent chemical bonding (e.g. biotin-avidin) or a combination of any of the above. In a preferred embodiment the binding agent is in the form of a magnetic or paramagnetic particle, comprising a binding moiety and the binding moiety is bound by non covalent chemical bonding (e.g. biotin-avidin) to the surface of the particle. Additional embodiments could also include physical adsorption, covalent chemical coupling, non covalent chemical bonding (e.g. biotin-avidin) or any combination of these to the surface of a magnetic agent, such as a magnetic particle. The magnetic agents/particles which are functionalised to comprise the binding agent bound thereto, may simply be deposited within a channel of the cartridge, such that upon the sample being applied to the cartridge and being drawn into the channel(s), the functionalised magnetic agents/particles are resuspended by the fluid sample and hence come into contact with any analyte in the sample. The area of deposition may be specifically defined using hydrophobic stop features, through the techniques described previously in order to separate this area from the detection area in order to ensure that high background readings are not obtained due to reagent components (e.g. fluorescent latex) being dried down in the measurement/detection area.

As mentioned above as well as the binding agents, the cartridge may comprise one or more further reagents deposited within said microfluidic channels(s), which reagents may facilitate detection of the captured analyte. For example said one or more reagents may include a label which has been adapted to specifically bind to the captured analyte, thus facilitating its detection.

Bound analyte may be detected directly providing the bound analyte is capable of generating a detectable signal, or upon binding of the analyte a reaction may place, so as to generate a reaction product and the reaction product may be detected. However, in a preferred embodiment, bound analyte is contacted with a label which is able to bind the bound analyte and a label/binding agent/analyte complex is subsequently detected. The label may itself be bound to a further binding moiety which is also capable of specifically binding to the binding agent/analyte complex. Typically the label is able to bind to a different portion of the analyte to which the first binding agent binds, or is capable of binding to a region of the binding agent/analyte complex which is formed only on generation of such a complex.

Bound analyte may be transported to the label within a region of the cartridge by way of the transport means in the reader causing the bound analyte to be moved. Alternatively a detection agent or label is brought into contact with the bound analyte by virtue of an amount of fluid being introduced into the cartridge from a fluid reservoir/reservoirs in the reader.

Desirably the binding agent and any detection agent/label are in a dry state when deposited in the channel(s) of the cartridge.

In one embodiment, the detection agent/label which is designed to facilitate detection of the analyte, is initially located upstream (in terms of the direction the sample flows into the cartridge following introduction) from such a stop feature. In this manner said detection agent does not initially come into contact with the sample upon initial sample application to the cartridge. Only when a fluid such as a buffer is provided to the cartridge through the fluid input port, is the detection agent constructed with the bound analyte. When a fluid is introduced into the cartridge from the reader, the detection agent may be carried by the fluid into contact with the bound analyte resuspended and carried by the fluid, passing by the stop feature and into contact with the captured analyte.

In another embodiment, after the initial binding phase between the sample and the binding agent and optional wash, the magnetic particle-analyte complex within a buffer media could be transferred to an upstream region of the channel, where the label is located, in dry form within the channel. The magnetic particle-analyte complex within the buffer media would resuspend/rehydrate the label and allow binding of the label to the analyte. This transfer event is possible due to the ability of the reader to effectively and accurately remove air from the channel (which is a sealed system). This method may allow greater control of rehydration of deposited reagents and homogeneity of reagent dispersion.

In another embodiment, the binding agent and the label are deposited in the sample channel. The sample rehydrates these reagents allowing the binding reaction to occur. In this embodiment all the reagents can contact the sample, the reader then accumulates the magnetic particle-analyte-label complexes to a region within the sample channel via the application of a magnet/electromagnet. The reader then expels the unbound label/sample into the sink using an air/fluid wash. The reader can use a disposable fluid/air reservoir/reservoirs or likewise a reusable fluid reservoir/reservoirs. The magnetic particle-analyte-label complex is then quantified in a fluid or air environment.

Each cartridge may be designed to carry out single analyte detection or multiple analyte detection. Moreover, each cartridge comprises more than one microfluidic channel system, so that more than one assay may be carried out using a single cartridge.

Desirably the cartridges may easily be mass produced. The cartridge may provide in a strip, where a number of cartridges are initially connected for example, be initially together, such as by way of a perforated seal. In this manner, the user can easily remove a cartridge from the strip, prior to use.

Once the cartridge has been loaded with a sample, any captured analyte may be detected by way of a suitable reader. The present invention provides such a reader and an important aspect of the present invention is the separate provision of a fluid/buffer reservoir/reservoirs within the reader. One advantage of this is that the cartridges themselves may be initially "dry", that is contain little or no fluid within the cartridge prior to sample application. This not only simplifies manufacturing of the cartridges themselves, but also improves shelf-life and allows many of the cartridges of the present invention to be stored at room temperature, with little degradation of the chemical or biological components within the cartridge prior to use.

In a further aspect there is provided a method of conducting an assay on a sample, the method comprising:

Introducing a sample into a microfluidic cartridge of the present invention such that any analyte present in the sample is capable of being bound by a binding agent;

washing any unbound material away from the bound analyte using a suitable fluid or gas introduced to the cartridge by way of the input port and;

detecting any labelled bound analyte present in the cartridge.

In a further aspect there is provided an assay system for conducting an assay on a fluid sample, the assay system comprising:
 a) a microfluidic cartridge according to the first aspect (or preferred embodiments thereof) and;
 b) a reader device, the reader device comprising:
 i) a receiving port for introducing the cartridge into the reader;
 ii) an internal reservoir/reservoirs for storing a fluid or a gas;
 iii) means for delivering the fluid or gas to the input port(s) of the cartridge once inserted within the reader, so that fluid or gas may be transported through the microfluidic channel(s) of the cartridge and;
 iv) detection means for enabling detection of any bound analyte or a reaction product formed as a result of the analyte binding the binding agent within the cartridge.

The reader includes a receiving port into which the cartridge is to be inserted. The reader may be adapted so as to ensure correct insertion of the cartridge and this could take a variety of forms. For example, the cartridge may be initially located on a carrier mechanism which enters the reader, such as may be found in computers for loading CDs and the like. Alternatively the receiving port may be sized to allow the cartridge to be received and an internal stop member may be found within the reader which the cartridge abuts once inserted correctly. Additionally, or alternatively, features found on or cut into the surface of the cartridge may be designed to co-locate with features found within the reader and only once the cartridge is correctly located in the reader, will the cartridge be able to be read.

The fluid reservoir/reservoirs is preferably sized such that more than one sample cartridge may be analysed and read before fluid in the reservoir/reservoirs needs replacing. Desirably many assays may be carried out before fluid in the reservoir/reservoirs may need to be replaced. Alternatively, in the case where the internal reservoir/reservoirs is filled with air, the reservoir/reservoirs will not require to be replaced as when the reservoir/reservoirs was completely expelled, it could retract to its starting position, drawing in air from the atmosphere. In the case of a fluid reservoir/reservoirs, the fluid may be introduced into the reservoir/reservoirs manually from another source. Preferably the reservoir/reservoirs takes the form of a replaceable cartridge, which may be introduced into the reader when required. For example, a user may have, or be provided with a reader which is able to be configured to carry out a variety of different types of assay, but the user is provided with a kit comprising assay cartridges and a fluid reservoir/reservoirs cartridge which are suitable for a particular analyte or analytes to be detected. In this manner, prior to use, the user inserts the fluid reservoir/reservoirs cartridge into the reader. The reservoir/reservoirs cartridge itself may have a unique identifier feature, such as a bar-code or chip device, which is recognised by the reader to be associated with a particular assay which is appropriate for the sample cartridges and reservoir/reservoirs cartridge, or the user may configure the reader to conduct a particular assay which is associated with the particular sample cartridge and optionally the reservoir/reservoirs cartridge. For some assays although differently manufactured sample cartridges may be required, a single fluid reservoir/reservoirs cartridge may be used to conduct a variety of different assays. Desirably a single fluid reservoir/reservoirs cartridge may contain enough fluid to be able to carry out many assays, such as greater than 25 or 50 assays, before the reservoir/reservoirs cartridge requires to be replaced. The fluid may be a washing agent such as water, which may include a buffer, such as PBS, HEPES and the like. Other fluids may also be suitable.

In the embodiment where the binding agent is bound to the surface of magnetic agents, such as magnetic beads, it is understood that the reader will comprise a permanent magnet or electromagnet which is designed to apply a magnetic field or be brought into close proximity or a magnetic field applied, in order to concentrate and hold the magnetic particles in a particular area of said microfluidic channel of the cartridge. This area may be the detection area. Concentrating the magnetic particles into a particular area may serve to facilitate detection of any captured analyte and/or increase sensitivity of detection. Moreover, by holding the particles by way of the magnetic field it also allows unwanted fluid surrounding the bound analyte to be washed away, thereby leaving the captured analyte free of potentially interfering agents/contaminants which may be present in the initial sample. The permanent or electromagnetic field may be reduced or increased, such as by moving a permanent magnet closer to, or further away from the cartridge, or by increasing or decreasing the intensity of the applied field. This may serve to allow the magnetic particles to "relax" or become less concentrated in a particular location, whilst still being held to a certain extent by the magnetic field or not. This may facilitate further reactions to be carried out on the particles, which may be conducted more efficiently compared to if the magnetic particles where tightly concentrated. It may also be preferred in certain applications that the detection is carried out when the particles are less "concentrated" or relaxed.

In use the magnet may be used to hold any bound agent once the magnetic field has been applied to the sample. Fluid from the fluid input port may be introduced into the cartridge and the fluid may wash any non-bound components of the sample away and/or allow other reagents such as a detection agent to be brought into contact with the captured analyte.

The reader of the present invention further comprises detection means for detecting any captured analyte within the sample cartridge. The detection means may be any suitable means depending on the particular assay. For example, the detection means may be a fluorimeter, which may be used to detect a fluorescent signal, once appropriately excited, from the labelled or unlabelled bound analyte or reaction product. The bound analyte/reaction product may naturally fluoresce once light of an appropriate wavelength has been used to excite the analyte/product, or a further label may be used to separately bind the bound analyte and the label detected by fluorescent means. Other labels which may be employed and hence the detection means adapted accordingly, include radiolabels, phosphorescent labels, colloidal metal particles, bioluminescent labels, colourimetric labels, electrochemical labels and the like. Moreover, as mentioned above the bound analyte or radiation product itself may be directly detected using techniques such as Raman spectroscopy and the like.

The detectable labels may be used alone, or in conjunction with a microparticle or bead, such as a metal oxide, polysaccharide or latex particle. Many types of latex and other particles are know in the art The reader comprises suitable means for transporting fluid from the fluid reservoir/reservoirs into and throughout the cartridge. The reader may also be configured to enable air, such as filtered air, to be transported into the said microfluidic channel(s) of the cartridge. The reader comprises appropriate tubing, valves and/or seals, as necessary, to enable fluid in the reservoir/reservoirs and/or air to be introduced into the cartridge. The means may be a pump/pumps and the pump may pump fluid/gas in one-direction, or may be able to pump fluid/gas back and forth. A preferred pump is a stepper motor linear actuator, piezoelectric pump, osmosis pump, peristaltic pump or piston pump. Fluid/gas delivery to the sample cartridge may be controlled by a microfluidic control assembly, which may control delivery or one or more fluids/gases to the sample cartridge, to one or more input apertures in the cartridge and at suitable time points.

The reader may include other features, such as a heating device to allow assays to be conducted at a particular temperature, as well as appropriate electrical circuitry and software to allow the reader to be programmed to carry out one or more different assays.

The platform system of the present invention, comprising cartridge and reader provides a number of distinct advantages:

1. Reduced Sample Volume: capillary introduction of a fluid, such as a finger stick blood sample, reduces the complexity for the user and allows the tests to be performed in any environment (e.g. ambulance, point of care, doctor's surgery, battle field etc), and similar to glucose testing, allowing products to be placed anywhere.
2. Performance, Sensitivity and Precision: The ability to perform multiple step assays will increase sensitivity, precision and reproducibility of assays, a major requirement of any IVD test. This will become more and more important as the FDA continues its reduction of the allowable total error for product launches of new IVD tests (entry into existing and new product markets will become harder).
3. Room Temperature Stability: Many existing IVD tests require refrigerated storage and shipping, this requirement adds significant cost to the product and also restricts the usage and distribution of the product. The initial "dry" nature of the sample cartridges aids in their stability and shelf-life.
4. Low material costs and a simple manufacturing process allow for low costs of goods (COGs), allowing substantial and increased profits to be generated by the sales of IVD strips. This is especially needed in the immunoassay and molecular IVD market where the conventional tests tend to be of high complexity driving both the strip material costs and overall assay cost higher.

DETAILED DESCRIPTION OF THE INVENTION

The present invention will now be further described by way of example and with reference to the figures which show:

Figure 1:
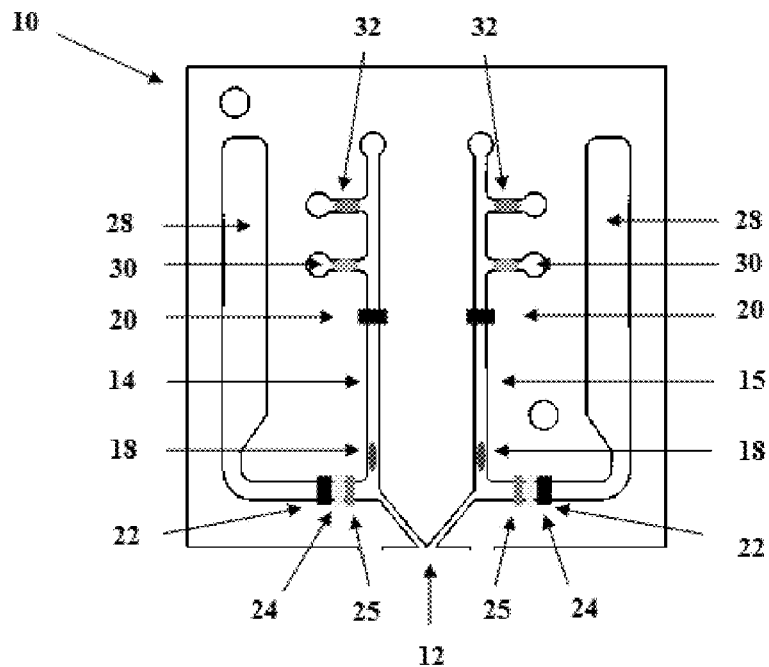
FIG. 1 shows a schematic representation of a sample cartridge in accordance with the present invention.

A sample cartridge (10) in accordance with an embodiment of the present invention is shown in FIG. 1. A fluid such as blood is applied to the sample introduction port (12) (via, for example, finger or venous blood). In this particular embodiment two channels (14,16) span from this one sample introduction port (12), the channels (14,16) are separate and are not joined, although to the user who is applying the blood the channel may appear as one. Although not to be construed as limiting, the further description will relate to the sample being a sample of whole blood.

The total sample application may be smaller than 1 µl depending on the number of channels to fill therefore when the user applies a sample, such as a drop of blood, both channels (14,16) will fill under capillary force. This process is very fast and more in tune with blood glucose strip filling as opposed to the lengthy blood separation filling of some immunoassay platforms. Deposited in the two channels (14, 16) are magnetic particles functionalised with antibody (18). As will be described in more detail, the blood fills each channel (14, 16) to the fluidic stop features (20, 22), one stop (22) downstream of a sink void (28) and the other stop (20) in the main sample channel. Fluidic stop features may be created by applying a printable hydrophobic ink to a surface of the channel. When the cartridge (10) is formed from three substrates (50, 52, and 54) as shown in FIG. 2b, the hydrophobic ink may be applied to top (50) and bottom (54) substrates, so as to form a stop feature on the top and bottom surfaces of a channel. The fluidic stop features (20, 22) in the main sample channel may also act as fill detect electrodes if made of a suitable hydrophobic electrically conductive material. As the cartridge (10) is inserted into the reader, a cartridge heating mechanism may be initiated, heating the cartridge to a predefined constant temperature for the duration of the test. This allows many benefits which are commented on hereinafter.

Figure 2:
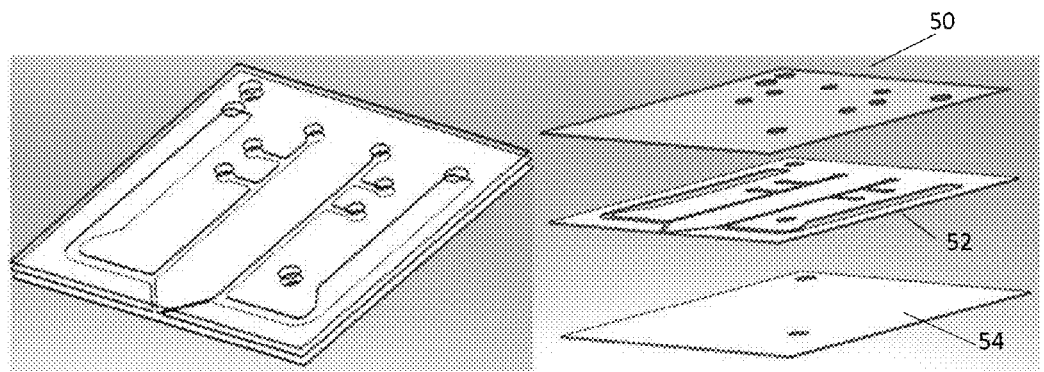
FIG. 2 is a schematic representation of how a cartridge of the present invention may be formed.

At the end of each of the 2 sample channels (14, 16) on the cartridge there may be an electrode (23), see FIG. 2. There may also be an electrode (23) present near the overflow sink (28) (which could also be used as electrochemical measurement zones). Through the reader, checking the electrical continuity between the electrodes, the reader will be able to confirm that the channels (14, 16) have been successfully filled with sample. This can be performed through a simple conductance measurement. For a specific channel, if the electrodes (23) have been successfully wetted with blood (meaning that both channels have been filled completely with sample) then an electrical current can conduct from one electrode to the other through the blood sample. Otherwise if the blood sample is not present, or has only partially filled the channel, then one of the electrodes will not be wetted, meaning the electrical current cannot flow from one electrode to another.

In the present cartridge/assay system, it shall be possible to measure the hematocrit of the blood sample. The design of the cartridge means that the measurement can be performed without any interference from the reagents that are used for the primary assay functionality.

Figure 3:
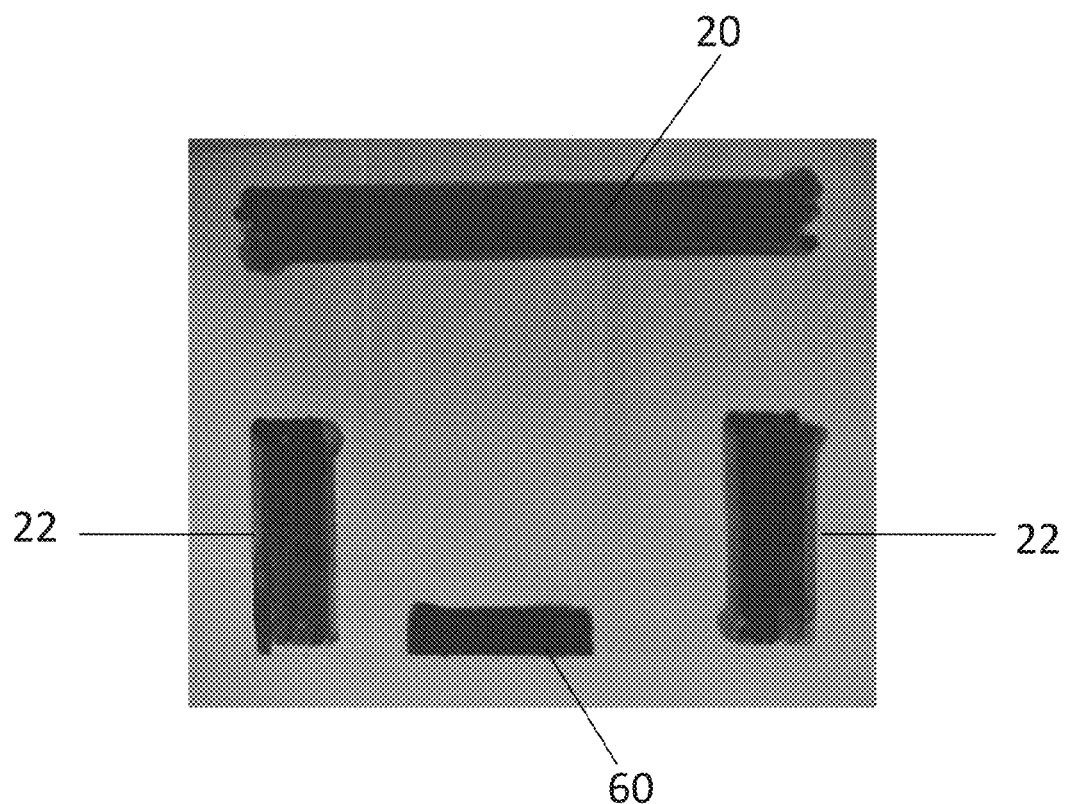
FIG. 3 is a photograph of a portion of a cartridge according to the present invention showing various features.

FIG. 3 shows a portion of the cartridge (1) in more detail and in particular the fluid stop features (20, 22). An additional feature (60) is shown adjacent to the sample application point (12). This feature (60) is designed to prevent any sample from wetting the outer surface of the cartridge upon sample application The hydrophobic stop features (20, 22) are present on both inner surfaces removing any hydrophilic path resulting in the fluid stopping at this feature. In one embodiment two hydrophilic surfaces are utilised however alternative combinations of hydrophilic/hydrophobic surfaces could be used to fill the strip by capillary action. In an extreme example of this two hydrophobic inner surfaces could be utilised and by providing a "sucking" action by way of a pump in the reader the cartridge may be filled with the sample.

Figure 4:
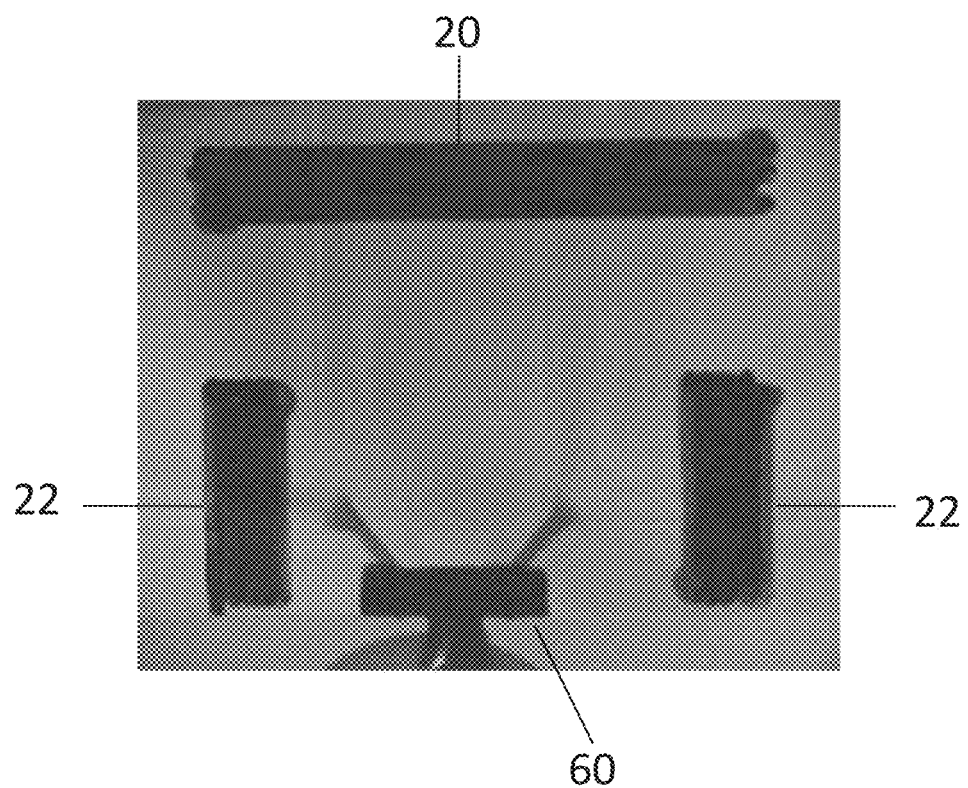
FIGS. 4 and 5 show blood entering and filling the portion of the cartridge shown in FIG. 3.
Figure 5:
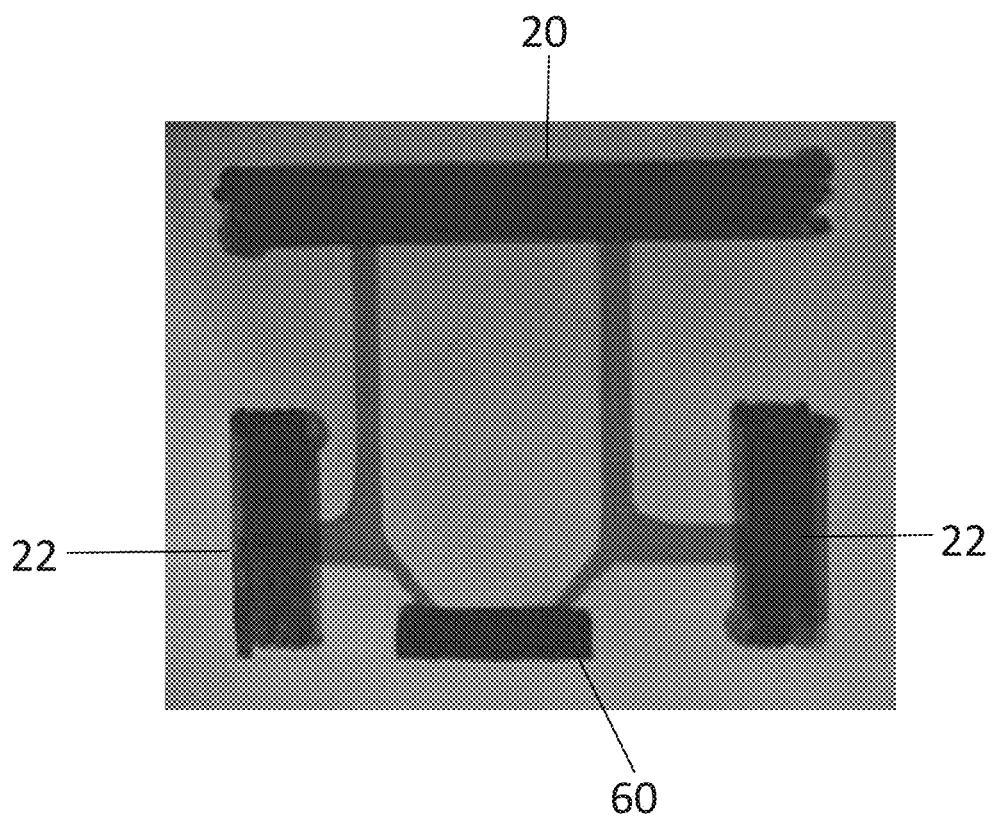

As the blood fills the sample channels (14, 16) (see FIGS. 4 and 5) the antibody functionalised magnetic particles (18) (which are pre deposited in the channel as dry reagents) are resuspended by the blood, thereby allowing binding any analyte/s present. The blood fills to the stop features (20, 22), see FIG. 5. Once the particles (18) are resuspended, incubation with the blood sample would be allowed to occur for a defined period of time (incubation time) and controlled by appropriate software and programming of the reader. Magnetic particles may be chosen as the capture phase due to their high mobility and functionality (size dependent i.e. diffusion coefficients etc) to reduce diffusion distances and ultimately incubation time. This type of reaction will be very efficient and reproducible at binding analyte from blood samples. During the magnetic particle binding of analyte, a hematocrit measurement may be performed by hematocrit electrodes (24). The hematocrit value can be used by the reader to calculate the final concentration of the analyte as the reference value will be a plasma measurement made by a clinical analyser. A hematocrit measurement may be required to correct for the concentration difference associated with analyte present in a given volume of sample due to differing ratios of red blood cells to plasma. Therefore a whole blood measurement may be corrected for this difference by means of a hematocrit measurement so that results are consistent with those associated with a plasma sample.

Figure 6:
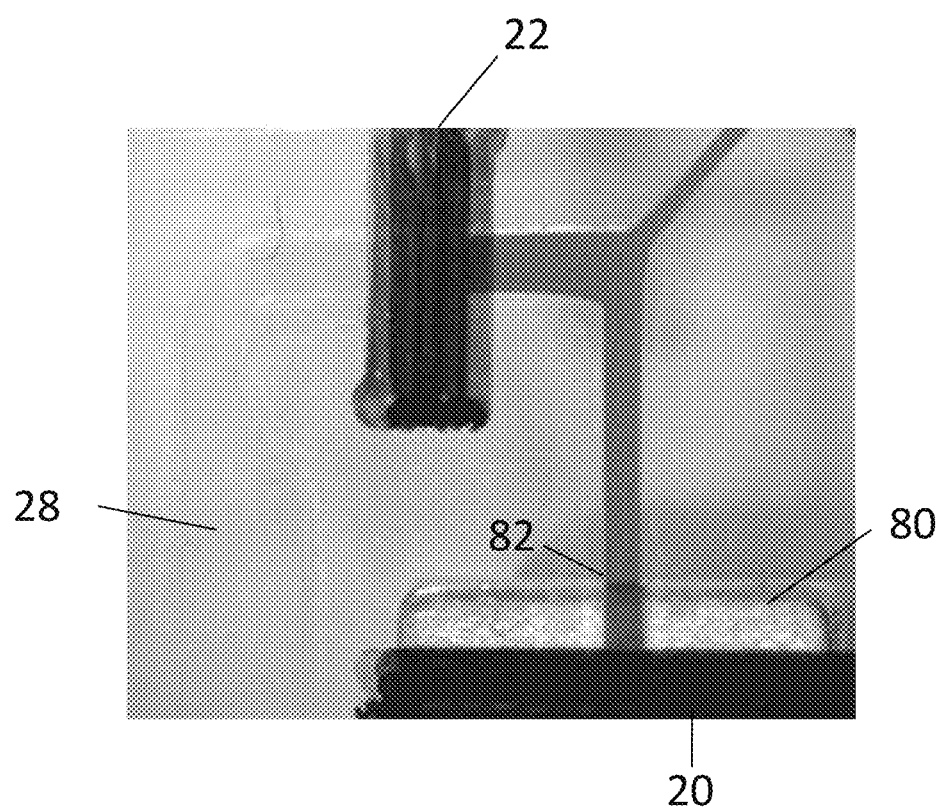
FIGS. 6, 7 and 8 are photographs of a detailed portion of a cartridge of the present invention showing magnetic particles being captured by a magnet and being retained following washing away of a blood sample.
Figure 7:
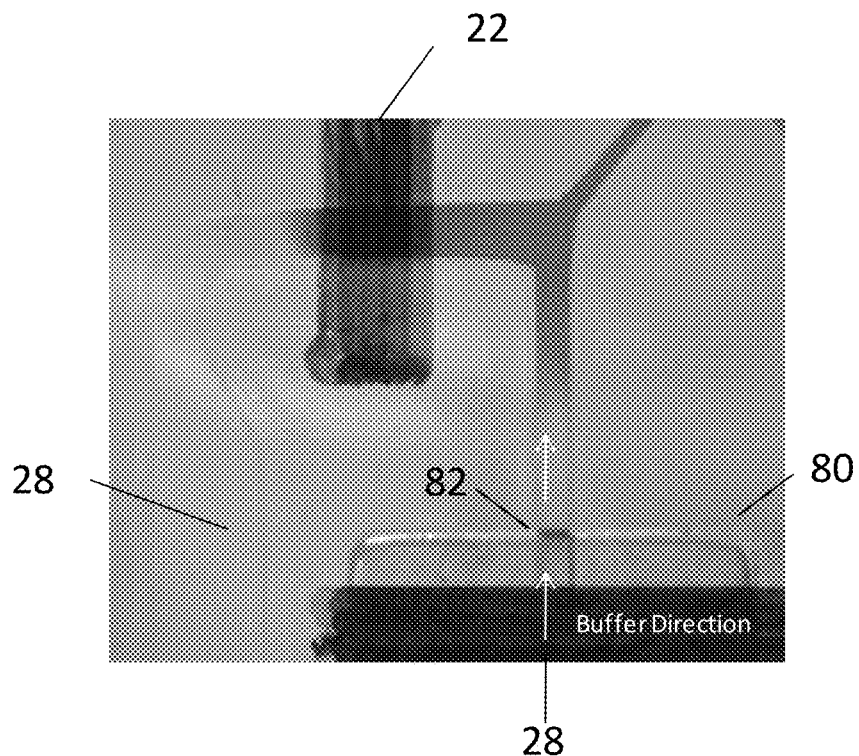
Figure 8:
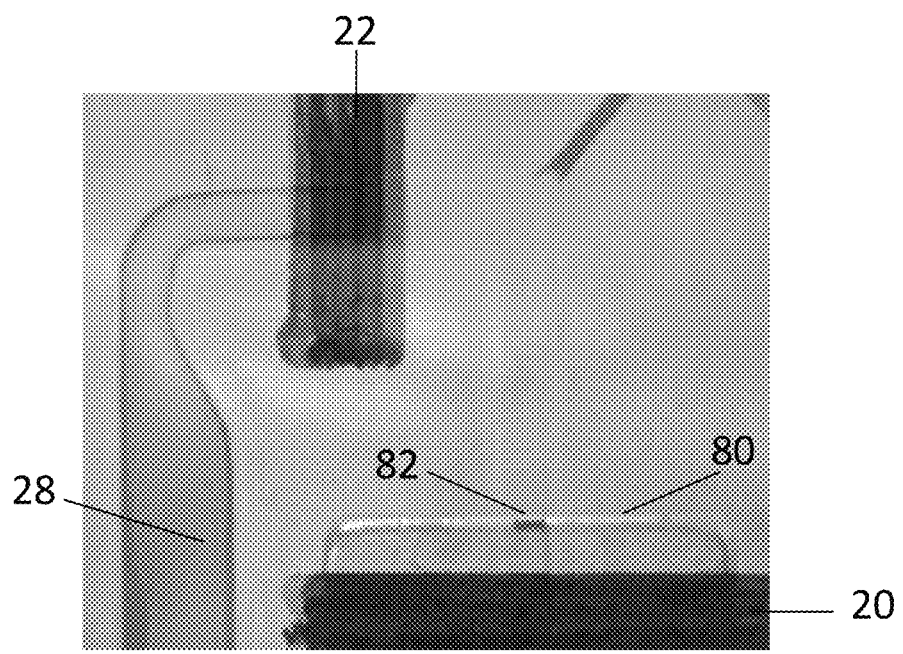

After the antibody functionalized magnetic particles (18) have bound any analyte in the blood a permanent magnet (80) or electromagnetic field is used to hold the analyte-antibody magnetic particle complex in place (see FIG. 6). A wash buffer or gas is then delivered from an inlet port (26). The wash medium is provided from a buffer reservoir/reservoirs present in the reader (a particular buffer reservoir/reservoirs and hence buffer may be inserted into the reader depending on the particular assay and hence analyte being detected). A defined volume of buffer (e.g. 1-2 µL) is expelled from the reservoir/reservoirs of the reader via a pump system into the sample channels (14,16) pushing the blood past the fluid stop feature (22) into the sink void (28), leaving the magnetic particles in buffer. (See FIGS. 7 and 8). The magnetic particles (18) can be visualised as a discreet band (82) still held within the channel (14, 16).

After this step a series of further wash steps, as above, may be performed (all using the magnetic particle holding step by an applied magnetic field) and where other deposited dry reagents (30, 32) may be resuspended in buffer (for example, the same buffer as the wash buffer) which is then pumped into the sample channels (14, 16), to allow binding events to occur in a very controlled manner. Or as previously described, the washed magnetic particle—analyte complex which is contained within the clean buffer matrix may be transported upstream, past stop feature (20) to the location in the strip where the label is dried down in the disposable test cartridge. At this point the magnetic particle—analyte complex can bind to the label followed by an additional wash step and measurement of the label. (In both of these examples only the magnetic bead-analyte binding reaction occurs in the blood, all the other reaction and/or binding steps occur in a very controlled buffer environment).

Figure 9:
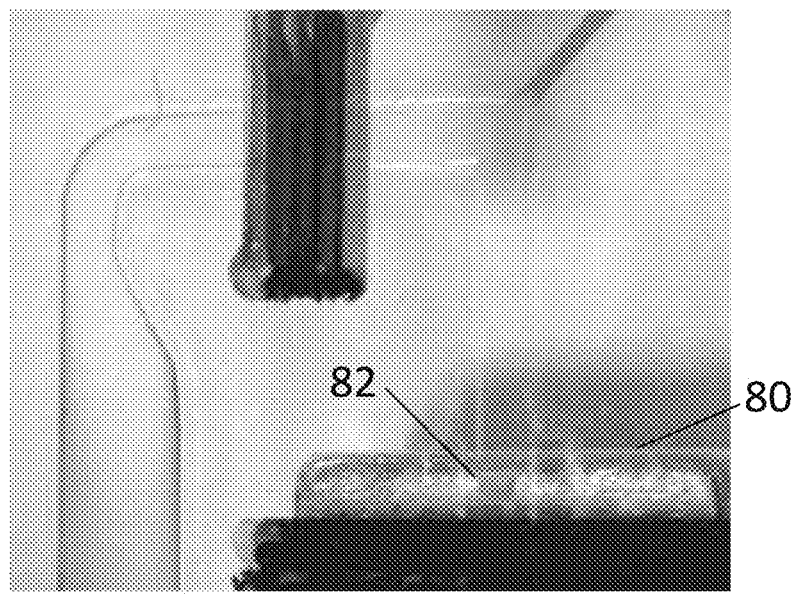
FIG. 9 is a photograph of a detailed portion of a cartridge of the present invention showing magnetic particles being held more diffusely following partial removal of a magnet.

However, the magnetic field may also be "relaxed" (see FIG. 9) by moving the magnet away from the cartridge and thereby reducing the magnetic attraction in this manner the magnetic particles (18) may still be held by the magnetic field, albeit less strongly and a more diffuse band (84) of particles may form. Moving the magnet (80) back towards the cartridge again will serve to concentrate the particles (18) once more.

In summary, this means that any reagents and/or labels never contact the "dirty" blood matrix, and all reactions/binding (other than the initial analyte capture step) is very controlled in a buffered, optionally heated environment to maximise detection efficiency and prevent/minimise non specific binding and interfering products to be removed (maximising the repeatability/precision of the measurement). This allows the present system to use reagents that would not have normally chosen because they were "problematic" in plasma/blood. In addition it also means all the detection measurements, such as fluorescent measurements also occur in a "clean" buffer environment meaning sample quenching/interference (as expected in blood or plasma) is reduced/removed allowing very sensitive reproducible measurements to be made. This allows a much greater choice of detection labels e.g. fluorophores, because quenching of excitation or emission light is minimised.

It should be appreciated that the foregoing description, with reference to FIG. 1, has been made in relation to a two channel cartridge, but the present invention also relates to single channel as well as multi-channel e.g. 6, 7, 8 etc cartridges. Each channel may carry out the same reaction for reproducibility/accuracy purposes, or may be designed to carry out different assays—in this way each cartridge may be capable of carrying out a "multiplex" reaction.

Figure 10:
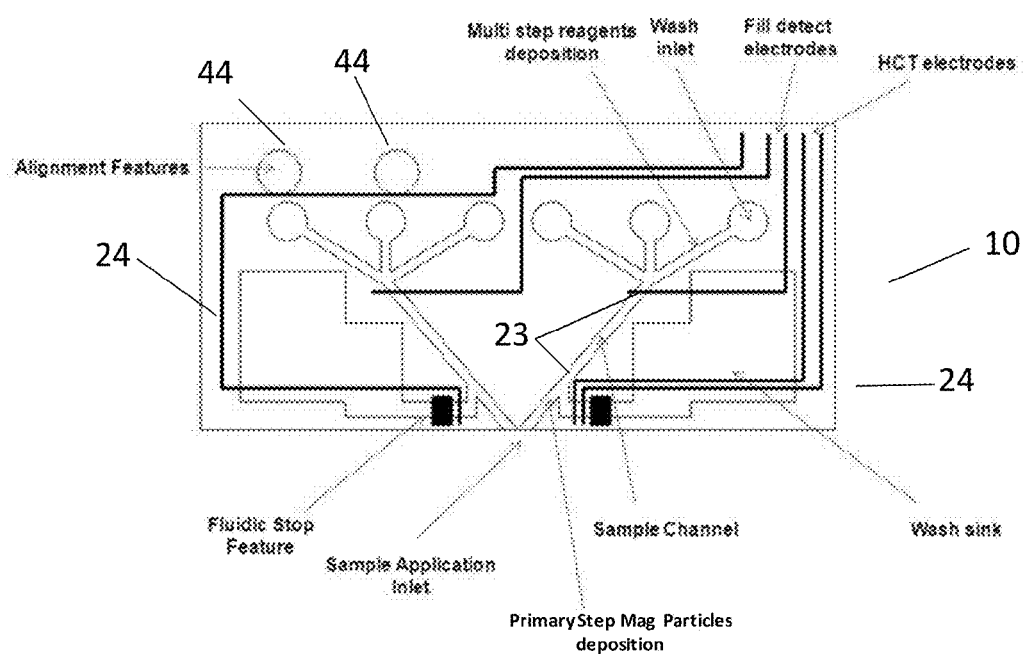
FIGS. 10 and 11 are schematic representations of further embodiments of a sample cartridge in accordance with the present invention.

FIG. 10 shows a similar cartridge (10) to that shown in FIG. 1, but additionally shows fill electrodes (23) which may detect correct filling of the sample by the cartridge (10). Further electrodes (24) are provided to enable a hematocrit value to be obtained from the blood sample.

Figure 11:
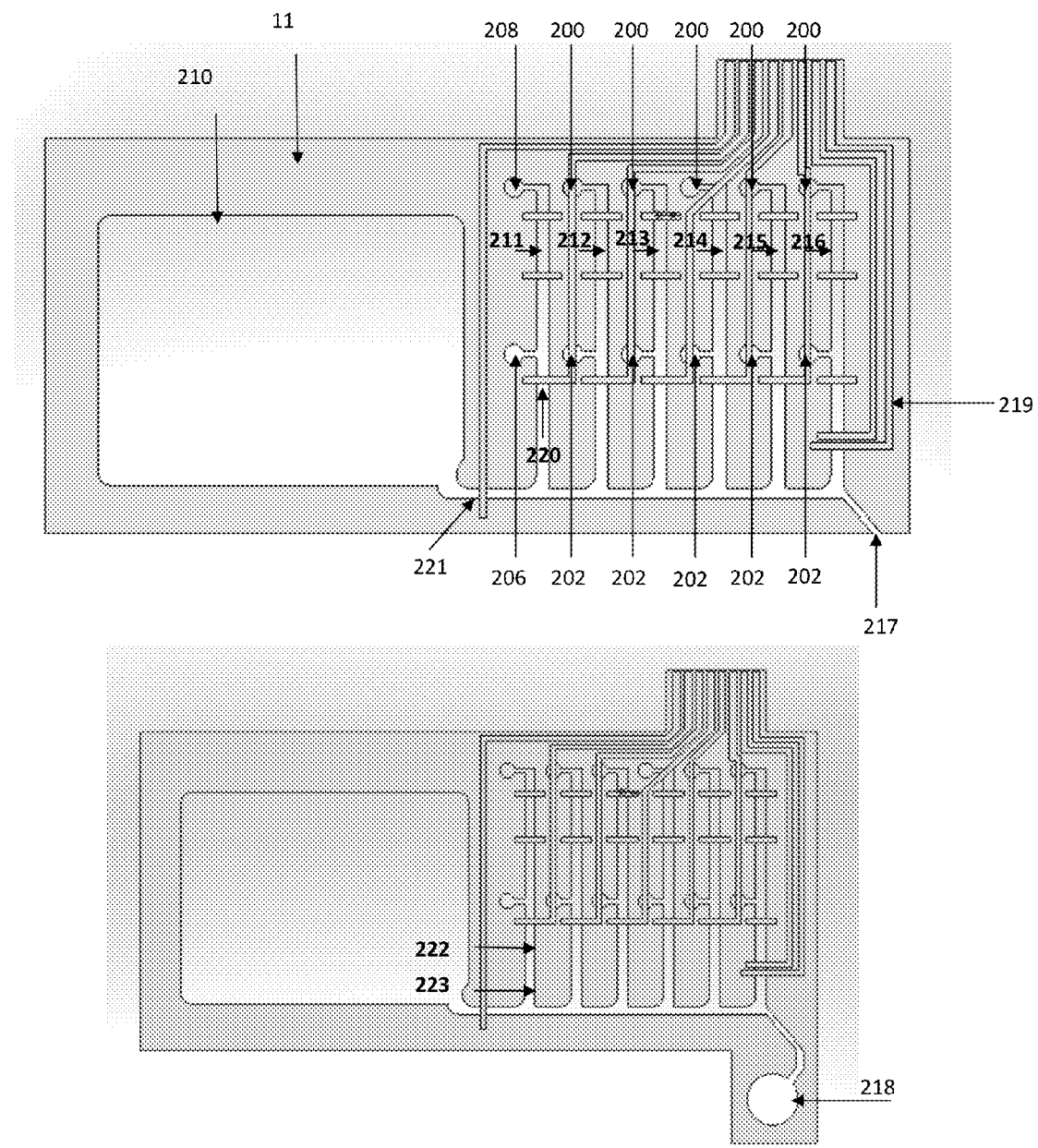

A further embodiment of a cartridge (11) in accordance with the present invention, is shown in FIG. 11. In this preferred embodiment 6 channels are fed by a single sample inlet port instead of the two channels being fed by the single sample inlet port. The 6 channel strip design is an expanded version of the 2 channel strip shown in FIG. 1 whereby additional channels have been added which all share the same sink (90). This allows a more effective use of strip footprint and allows increased multiplexing capacity.

Figure 26:
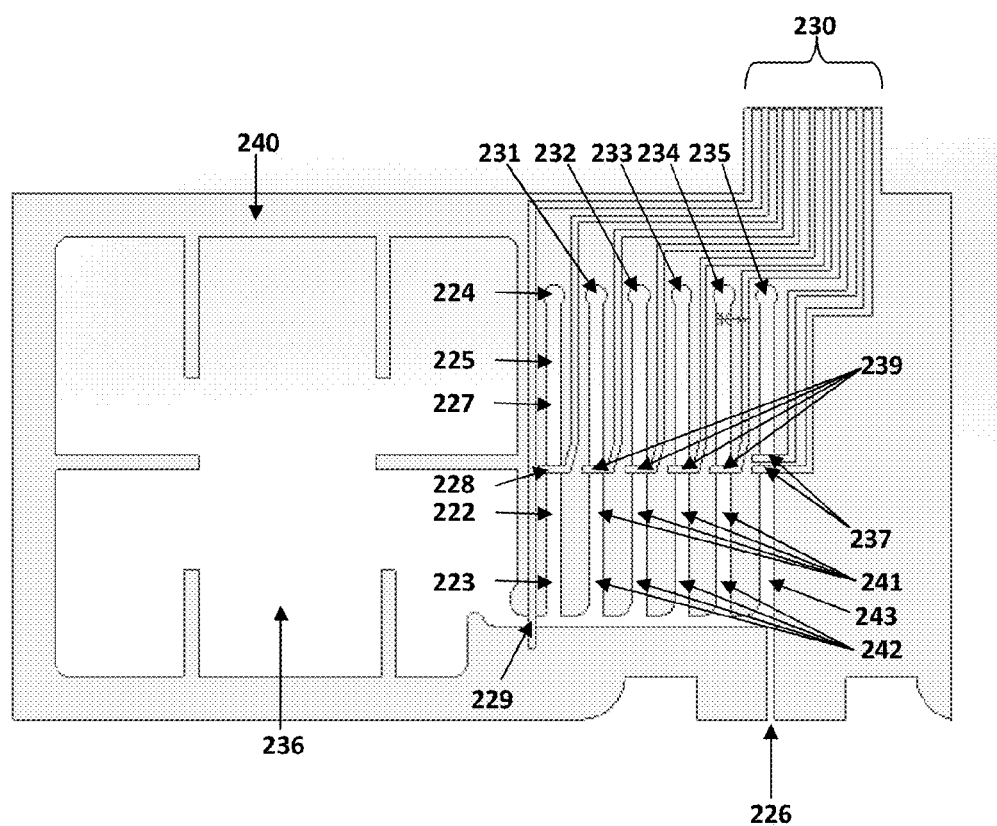
FIG. 26 shows a schematic representation of further embodiments of a sample cartridge (MST pro strip V1, as used in the experimental section) in accordance with the present invention.

Ultimately a measurement is made (e.g. fluorescent) by a reader using optical or other detection means, suitable for the label to be detected. For example, if the label is a fluorescent label the detection means may be able to perform and detect the excitation and emission of the chosen fluorophores: a schematic view of a hand held reader in accordance with the present invention is shown in FIGS. 12-15. This embodiment of the reader (MST Pro Meter V1) is the specific embodiment that was used to perform the experiments as described in the Experimental section. In addition all experimental results were obtained using the 6 channel strip design (as shown in FIG. 26). The reader (100) comprises a platform (106) for receiving and holding a cartridge (10) of the present invention and a sealing head (105) the actuation of which can be controlled by solenoids (108) for the purpose of producing a sealed system whereby the instrument can pump either a gas, such as air or a fluid such as a wash buffer into the strip in a controlled manner. Additionally the reader comprises a fluid reservoir/reservoirs cartridge (111) for holding fluid or gas for subsequent delivery to the cartridge (10). The reservoir/reservoirs cartridge may contain a separate chamber for each test channel contained on the strip such that the fluid/air actuation and control for each test channel is driven directly from what is effectively a separate pump source. Alternatively the reservoir/reservoirs cartridge may comprise of one chamber which is then split into multiple outlets such that the fluid/air actuation and control for each test channel is driven from a common pump source. The fluid or gas is delivered by way of an actuator (113) acting on the reservoir/reservoirs cartridge. There is also provided suitable optical detection means (107) and electrical circuitry (112) and an associated computer chip or chip(s) and software for controlling the reader and conducting the assay. In addition because the described system has the flexibility to perform many wash and reagent delivery steps many assay formats can be configured using the current system.

Figure 25:
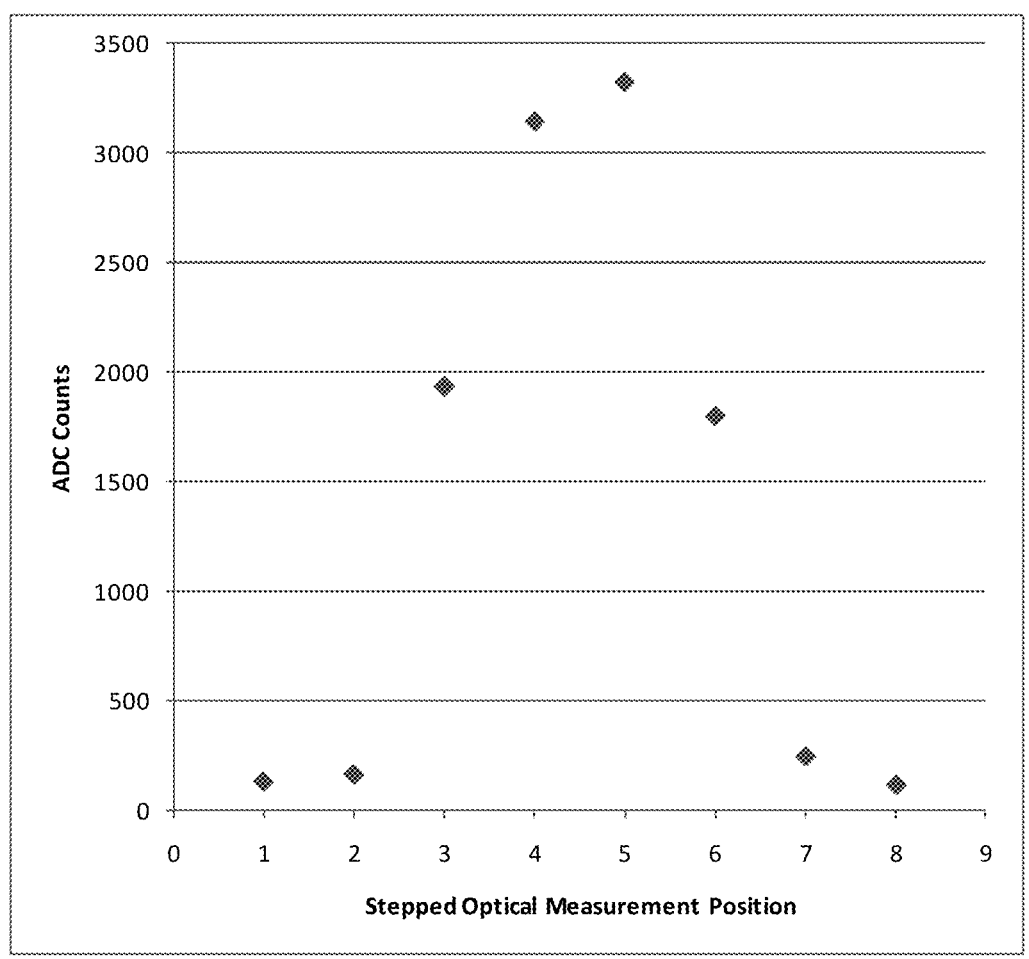
FIG. 25 shows graphed experimental results of a scan across a test sample channel in the strip MST Pro Strip V1 using the instrument MST Pro Meter V1.

A magnet holder (103) and associated magnet which may be orientated at 45 degrees, (104) can be controlled through the use of a motor (110) in order to bring the magnet in contact or close proximity to the test strip, for the purpose of influencing magnetic or paramagnetic particles contained within the test strip. In order to perform the assay measurement (e.g. fluorescent) the optical reading head (107) can be moved along the measurement or detection zones (222) of each of the multiple test channels in the test cartridge controlled by a motor (109). Thus the optical reading head can be utilized to perform multiple measurements across one disposable test cartridge. The plot shown in FIG. 25 shows the results of an example read of the optical reading head across a test channel in the test cartridge. (using the reader design MST Pro Meter V1). From the results it can be seen that the instrument can make multiple measurements across the width of the test channel allowing the peak fluorescence signal to be identified and transformed into a result through the use of an algorithm and displayed to the user through the LCD (101). In addition the instrument could interpret the shape associated with the measurements taken across the test channel and use this as an on board control, for example if the read response gives the shape of a steady decay or steady increase instead of a parabolic response then it could be used to determine an erroneous or non uniform result.

Figure 14:
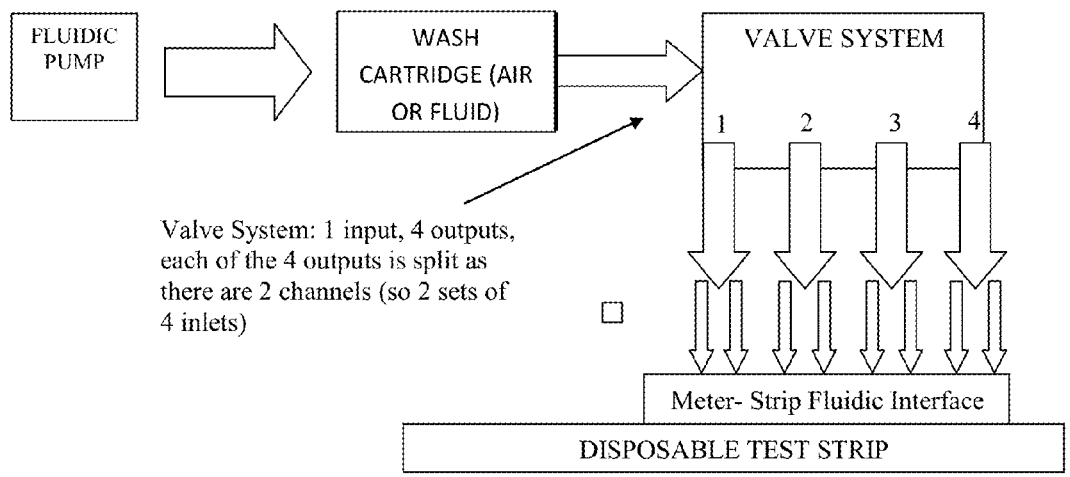
FIG. 14 is a schematic representation of a fluid management system found within a reader device of the present invention.
Figure 14:
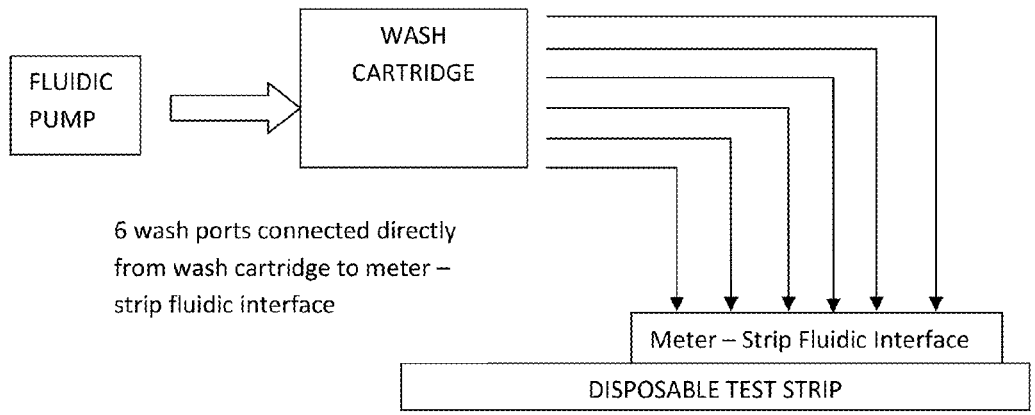

It will be appreciated that the reader is required to very accurately control the fluid/gas delivery of for example, the buffer wash to the disposable cartridge. The cartridge may involve a number of separate sample channels, and a number of wash steps may be required for each channel, with each wash step having to be conducted at a precise flow rate and with a precise volume. Each channel may have a plurality of wash interface ports ((26) of FIG. 1) over which a seal is made in order to ensure the correct delivery of the buffer/gas wash from the reservoir/reservoirs in the reader. A suitable fluidic management system may be made up of 3 main components (as shown in FIG. 14), a fluidic pump/pumps (113), a buffer reservoir/reservoirs cartridge 111 (and FIG. 15) and a reader/cartridge fluidic interface or seal (105).

The fluidic pump/pumps that is used to transport the fluid from the buffer reservoir/reservoirs cartridge to and throughout the cartridge, may be a stepper motor linear actuator (for example E21H4U-5-900 Haydon Kerk Motion Solutions), the features associated with a stepper motor linear actuator that make it a desirable solution include the fact that it locks in position when stopped (so that the fluid cannot push back against the buffer reservoir/reservoirs cartridge and linear actuator) and that stepper motors have movement of very fine resolution (e.g. 0.0015 mm/motor step).

The reader/cartridge fluidic interface may be achieved by using a soft rubber coated sealing head in the reader that co-locates with said wash inlet ports (26) of the cartridge. Alternatively a rubber gasket could be located on the disposable test cartridge, or there may be a rubber gasket present on both the sealing head and the disposable test cartridge. The sealing head will have an outlet (e.g. a hole in the rubber membrane containing the outlet from the fluidic management system) that lines up with each of the cartridge fluid input ports.

The reader may preferably include a buffer wash reservoir/reservoirs. The buffer wash reservoir/reservoirs may contain the buffer wash fluid for carrying out assays on a number of cartridges. Alternatively, in the case where the reservoir/reservoirs is filled with air, it could be a permanent feature of the reader design as it would not need to be replaced as has been explained previously.

Figure 15:
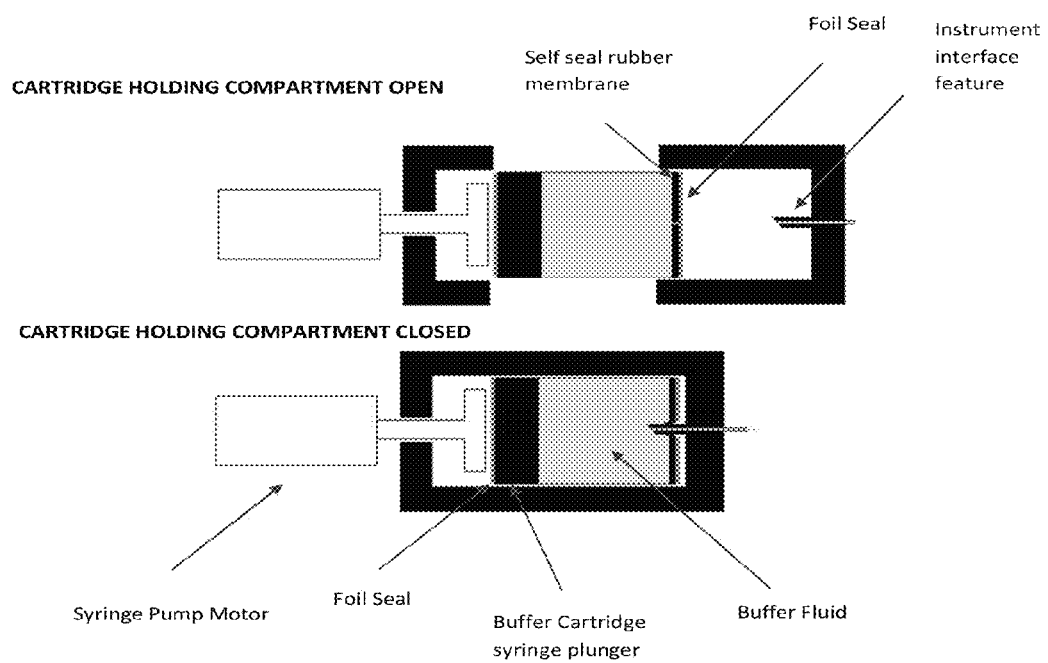
FIG. 15 shows a schematic representation of a fluid reservoir/reservoirs system and how this may be used within a reader of the present invention.
Figure 15:
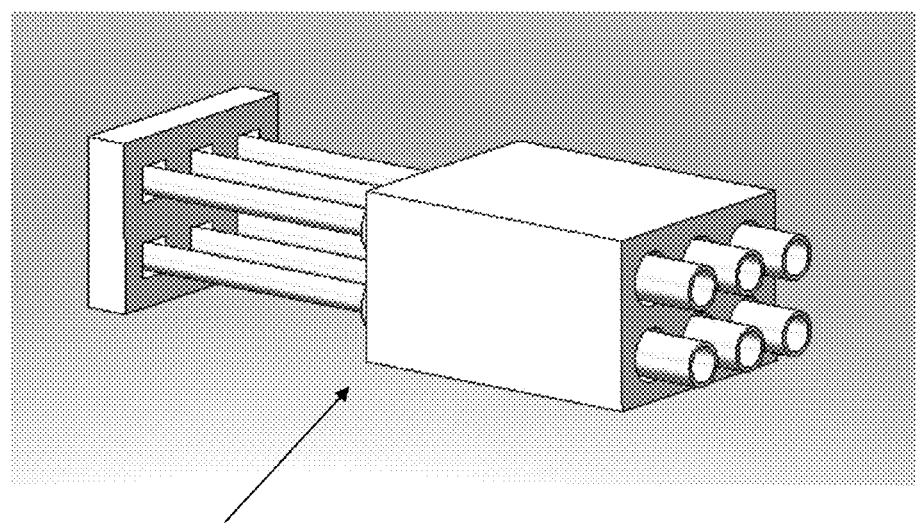

In order to make the reader suitable for use by the user, such that replacing the buffer reservoir/reservoirs cartridge does not result in the fluid spilling out and over the reader or user, the buffer/gas wash reservoir/reservoirs cartridge and the reader may be designed to have self sealing interfaces, such that when the reservoir/reservoirs cartridge is removed from the reader any fluid is sealed within the confines of the reservoir/reservoirs and the instrument. The seal may be designed such that it only opens when the reservoir/reservoirs is inserted correctly into the appropriate interface point in the instrument, a feature may be incorporated to penetrate the self sealing buffer reservoir/reservoirs cartridge. To ensure that the buffer fluid inside the buffer wash reservoir/reservoirs cartridge does not evaporate, which would lead to the formation of air voids within the cartridge, the buffer reservoir/reservoirs cartridge may have foil seals at both ends, over a syringe plunger end, and over a self sealing seal end. These foil seals will be broken by the syringe pump driver and the meter cartridge interface feature respectively. An example of such an embodiment is shown in FIG. 15, where the reader/sample cartridge fluidic interface is achieved by using a soft rubber coated sealing head in the reader that interfaces with the sample cartridge. The sealing head will have an outlet (i.e. a hole in the rubber membrane containing the outlet from the fluidic management system) that lines up with each of the strip inlet points.

The buffer/gas reservoir/reservoirs cartridge may have a singular chamber which drives the various wash steps associated with each test channel from a single source which is then split into multiple exit port points through various valves and tubing. Preferably the buffer/gas reservoir/reservoirs cartridge may have a separate chamber for each test channel such that the wash steps associated with each test channel are driven from individual sources. This type of design is also shown in FIG. 15, and does not require any valves in the reader or test cartridge. Alternatively the reservoir/reservoirs cartridge may have a number of chambers which are associated with common sub set groups of test channels contained in the test cartridge.

As discussed above in order to keep the capture phase and bound analyte etc from getting washed away during the buffer wash and reagent wash steps, the magnetic beads in the disposable test strip require to be held by the reader. This function will be fulfilled through utilising either a permanent magnet or an electromagnet. It is possible to manipulate the magnetic beads in certain ways that could help improve the accuracy, sensitivity and range of the measurement. For example for lower assay fluorescent signals, it may be beneficial for the magnet to gather all of the magnetic beads into a tightly bound clump, increasing the density of the fluorophores present and so the intensity of the light emitted towards the detector. In contrast in cases where there are higher signals, and the light sensor and reader electronics are close to saturation it may be beneficial to remove or move the magnet so as to relax or spread the magnetic beads over a certain area, thus reducing the intensity of the light emitted towards the sensor. This could be seen as a novel way of using the magnet to influence both the sensitivity and the range of the assay or affecting the binding kinetics of the multi-step assays. Typically for a magnet, the points where the flux density is highest (and so where the magnetic beads will tend to gravitate toward are along the edge of the magnet as this is where the magnetic flux lines have the shortest travel path from the north to the south pole.

It is a physical feature of assay development that the ambient temperature can influence the magnitude of response. In the present invention, this temperature effect will primarily be driven through the effect of temperature on diffusion, whereby an increase in temperature can result in increased binding efficiency between the magnetic beads and the target analyte, and the subsequent binding to delivered reagents. The present system may be used, for example in a doctors office and home use, and the range of temperatures the system may be exposed to will be broad, from perhaps as low as 10 Celsius to as high as 35 Celsius. One method of removing this temperature effect is in the heating of the test strip to a pre determined temperature, for example 40 degrees, this would remove any variation associated with the assay due to temperature effects. Thus, the reader may also comprise temperature control means, such as a heater.

The temperature control of the cartridge can be implemented by utilising the top surface of the optical block (which will be in contact with the strip and may be made from a heat conducting metal, such as aluminium, which has good thermal conductivity properties) as a heater in order to maintain the temperature of the sample cartridge. Alternatively the support platform on which the disposable test cartridge rests within the reader could be utilized as the heated surface that contacts the strip. The heating of the heated surface can be performed using a high wattage, low value (e.g. 1 ohm) resistor, or though using a MOSFET with the heatsink tab of the MOSFET attached to the optical block top surface. The temperature may be controlled by placing a temperature sensor on the heating block surface and using the output of this temperature sensor to modify the current flow through the high wattage resistor/MOSFET. One additional advantage of this implementation is that the MPPC silicon photodiode gain (The MPPC silicon photodiode is the detector used to measure the intensity of light emitted by the target fluorophores in the test strip) is sensitive to ambient temperature, therefore implementing the optical block top surface as a heater would also ensure that the ambient temperature in proximity to the MPPC silicon photodiode is controlled.

An alternative method of heating the sample cartridge would be to create a very thin heating element. The fact that the heating element would be very thin (100-250 microns) would also mean that a magnet could be positioned underneath the element and still be in close proximity to the cartridge so that the magnetic beads can be gathered. The thin heating element could take the form similar to that of a flexible PCB, with copper tracks sandwiched between two polymer layers. One side of the layer could then be coated with a reflective material, or a have a reflective layer adhered onto it to make the mirrored surface if the heating element were required to reflect light emitted from the target fluorophores back towards the MPPC silicon photodiode. Alternatively, in the event that background fluorescence becomes an issue in the system, one side of the element could have a matt black finish as opposed to a reflective surface.

The Optical block of the reader of the present invention may be capable of providing the light sources for multiple fluorophore excitation wavelengths and measuring the subsequent emitted light from the fluorophores. It is the intensity of this light emitted from the fluorophores in the disposable test cartridge that will provide the assay measurement. The Optical Measurement Block is responsible for measuring the amount of target analyte present in the cartridge through the associated bound labels, such as fluorophores. The Optical measurement block may comprise a multi pixel photon counter (MPPC) silicon photodiode (for example Hamamatsu S10362-11-100C) and a high power wideband LED which emits a broad spectrum of wavelengths (for example HP803WW Roithner LaserTechnik GmbH).

A MPPC silicon photodiode may be preferred as it has a very high internal gain (in the region of 1 million) compared to a standard photodiode (gain=1) or an avalanche photodiode (gain=in the region of 100). One convenient feature of the MPPC silicone photodiode is that its internal gain varies in relation to the reverse bias voltage that is applied to it (for example a bias voltage of 70V results in a gain of approx 1 million while a bias voltage of 65V results in a gain of approx 100,000). This relationship can be used by the reader to manipulate the dynamic range of the measurement system, i.e. for higher analyte concentrations the photodiode bias voltage can be reduced to ensure the photodiode output does not saturate the instrument electronics. It should be noted that in alternative embodiments a standard photodiode or an avalanche photodiode could be implemented in place of a MPPC silicon photodiode.

A high power wideband LED is convenient so that a single LED can be used to generate multiple excitation wavelengths (i.e. the light that is incident on the target analyte fluorophores) through having a filter slide that can be moved to place different filters in front of the LED to generate different wavelengths. The filter slide also contains filters associated with the silicon photodiode in order to block out the excitation light so that the silicon photodiode measures only the light emitted by the fluorophores.

With reference to the 2 channel cartridge as shown in FIG. 1, the Optical measurement block may be arranged such that there are 2 sets of LED and silicon photodiodes, one for each channel in the strip. The location of the photodiodes and LEDs are fixed. The filter slide can be moved such that different filters can be placed between the LEDs and the MPPC silicon photodiodes for different measurements. Alternatively, instead of having 2 fixed sets of LED and silicon photodiodes, there could be a single optical head implemented that can move between the different test channels.

Alternative embodiments of the stated configuration of the optical block are as follows:
1. In one embodiment, both the excitation source and the emission detector are located on the same face of the cartridge. An alternative to this is that the cartridge is sandwiched between the emission source and the emission detector.
   A reason that the source and detector may be located on the same surface is to allow space for the integration of the cartridge with the fluidic management system, cartridge connector interface, heating block and magnetic particle control.
2. In another embodiment, there is the implementation of a movable filter slide to allow selectivity in the excitation and detection of a number of fluorophores. In a simpler configuration where only a single fluorophore per channel is required to be detected, the filter slide would not be required and could be replaced with a single, fixed excitation filter and a single emission filter for each channel.
3. In a further embodiment, the light source for the excitation of the fluorophores comes from a broad band emitter. Alternative implementations where there is not the need to excite at multiple wavelengths could include wavelength specific light sources such as narrow band LED's.
   Another alternative to a wideband LED would be a xenon flash lamp, the intensity of a xenon flash lamp is much greater than that of an LED. In addition a xenon flash lamp emits over a larger range of wavelengths. Where broad band 'white' or 'warm white' LEDS can emit down to a wavelength of around 400 nm, xenon flash lamps can emit down to around 200 nm meaning that xenon flash lamps can be used for excitation wavelengths in the UV range.
4. In another embodiment, the optic block configuration could comprise of directing the excitation light at a dichroic mirror (or beamsplitter) mounted at an angle of 45 degrees to the normal which reflects the excitation light through 90 degrees towards the sample in the disposable test cartridge. The dichroic mirror is chosen such that the excitation light generated by the fluorophore is at a wavelength that travels through the dichroic mirror (i.e. is not reflected back towards the emission source) where the silicon photodiode is situated for detection of the emitted light. Additional optical filters may also be placed in front of the light source and optical detector in this configuration in order to narrow the pass band of light wavelengths produced by the emitter and accepted by the detector.

Due to the variation in processes associated with the manufacturing of disposable assay test cartridges it is normally required for each batch of cartridges to be characterised and for specific calibration values to be entered into the reader so that the assay response generated by the test cartridge can be normalised by the reader internally before the final assay result is reported. In the present invention, there exists the opportunity to utilise the buffer cartridge as a tool for transporting particular data of interest, for example assay calibration parameters about its associated batch of cartridges. One implementation could include the attachment of an EEPROM memory chip to the reservoir/reservoirs cartridge, whereby the data in the EEPROM memory chip can be read by the reader.

In one particular embodiment, the sample cartridge and associated reader are designed for carrying out an immunoassay, where the analyte to be detected is an antigen and the binding agent is an antibody. Paramagnetic particles may be functionalised by attachment of antibodies against either free or free and complexed antigen.

Due to the present cartridge design, importantly the only binding reaction that occurs initially is the antibody binding to any antigen in blood, this results in a number of advantages. Primarily it means multi-step assays can be performed, meaning the chosen label molecule/particle never contacts ("sees") the blood. This is a significant benefit over existing POC immunoassay technologies whereby both capture phase and label are in contact with the sample. The typical POC immunoassays binding schemes generally consist of either planar or magnetic capture particles and a label which could be bound to a particle, conjugate or polymer etc. However, both capture and label phase contact the sample (blood, plasma etc). This can lead to a number of problems. Within immunoassays there are many species that interfere with the immunoassay binding steps. Prime candidates are human anti-animal antibodies such as Human Anti-Mouse Antibodies (HAMA), animal anti-animal antibodies (in the case of veterinary applications), rheumatoid factor, anti-BSA antibodies, fibrinogen etc. Specific non-specific binding (HAMA, rheumatoid factor) and non-specific binding can result in highly inaccurate results resulting in poor performance and ultimately inaccurate diagnosis of patient samples. This is especially true as POC immunoassays are generally referenced to clinical analyser performance which incorporate multi-step assays, very effective wash steps and label detection in a clean matrix. Both specific non specific and non specific binding results in label bound to the capture phase in a manner not consistent with concentration of analyte (can be higher or lower than the expected result) resulting in an inaccurate result. Fluorescent latex particles may be employed which are functionalised by attachment of antibodies against free and complexed antigen. Thus a sandwich may be formed between the magnetic particles, antigen to be detected and fluorescent latex particles.

In one embodiment of the present system however, the detection label, such as a fluorescent moiety never contacts the blood, as the blood is washed away prior to any label being brought into contact with the bound analyte. Therefore any of these matrix events that could facilitate the non specific binding cannot occur because the magnetic beads (18) and detection label are not present in the blood at the same time, just like some clinical analyser systems. This is very important when considering the Allowable Total Error (ATE) of an immunoassay. There is a drive within regulatory authorities, such as the FDA to tighten the ATE on any new assay products to increase the accuracy of tests with respect to the reference systems.

For a given population of clinical samples, even if the majority of the bloods/samples recover accurately the ATE can be heavily affected by a few inaccurate responses. It is therefore very important that any new platform technology is designed to minimise these effects. The present invention aims to do that appropriate design of the cartridge and associated reader, thereby reducing sample to sample bias (e.g. elimination of specific non specific binding and non specific binding).

Another advantage of only performing the magnetic particle capture step in the untreated sample, such as blood is that blood measurements can become very accurate. Most immunoassays are highly sensitive with regards to reagent concentrations (i.e. concentration of the capture phase and label phase). Sufficient reagent concentration is required to drive slope whilst too high a reagent concentration results in increased assay intercepts. In a whole blood assay this problem can be further exaggerated as even if you deposit exactly the same reagent volume and concentration, the reagents will have different concentrations in different hematocrit bloods (as the reagents will resuspend in different volumes of plasma). For example, the same deposited reagents in a 60% hematocrit blood will have 1.87 times less volume than a 25% hematocrit blood. As a result the reagents will be more concentrated in the 60% hematocrit blood than in the 25% hematocrit blood. This alone could cause blood to blood bias problems as both the capture and label phase will vary in concentrations, therefore the overall capture efficiency (number of capture phase-analyte-label phase interactions made out of the total number of capture phase-analyte-label phase interactions possible=capture efficiency) will vary between bloods due to hematocrit effects alone. This further coupled with the varying viscosities of different bloods (and plasma's) affects the diffusion coefficients of any mobile reagent which can result in poor ATE.

Having only the magnetic particles binding analyte in the blood helps to significantly reduce this problem as the highly mobile and functional magnetic particles will be highly efficient with regards to binding the analyte. Therefore the magnetic particle concentration difference in high or low hematocrit bloods is less important as nearly all the available analyte is bound in this step. The blood to blood viscosities effects are further minimised by the applied cartridge heating, as there will be no temperature effect as the cartridge will always have a constant temperature as previously described.

For an immunoassay once unbound agents in the blood have been actively washed out of the sample channel out into the sink, the reader then delivers a small amount of buffer into the sample cartridge through a buffer inlet point on the strip containing either a dry deposition of antibody functionalised fluorescent latex bead (or other secondary binding reagents). The antibody labelled fluorescent latex bead is resuspended by the buffer and then pumped into the channel containing the magnetic particle-analyte complexes. The permanent magnet or electromagnet housed in the reader is still applying a magnetic field at this point and "holding" the magnetic particle-analyte complexes in place in the channel. Once the antibody functionalised fluorescent latex has been transported by the reader into the channel containing the magnetic particle—analyte complexes, the magnetic field is removed allowing a second binding reaction to occur. (Though it would also be possible to allow the binding phase while the magnet is in place and the magnetic beads are held in place). Alternatively the magnetic particle—analyte complex could be transported upstream in the sample cartridge, to contact the label. Alternatively as previously described all the binding reagents (magnetic particle capture phase and label) could be deposited in the sample channel and the binding reaction would occur in the sample channel. The magnetic accumulation and air/fluid wash by the reader ensures the magnetic particle-analyte-label complexes are quantified in an air/fluid environment.

The flexibility of the present system allows the potential for a very flexible and sensitive measurement. The whole system at this point is set up for high capture efficiency resulting in very sensitive assays as the magnetic particles are effectively preloaded with analyte, therefore collisions with .label .should result in successful binding events. For clarity a binding scheme will be described, however due to the flexibility of the present platform design nearly any assay architecture conceived can be formatted.

A wash step is generally performed to remove any unbound label Subsequent optical measurement is then made in a 'clean' environment. In the case of fluorescent detection, this allows the use of fluorophores which would not be usable in some matrices (for example blood) where significant quenching of the specific signal would (without removal of this matrix) otherwise occur.

Further amplification of signal if needed could be delivered if required by resuspending and pumping a tertiary binding reagent into the channel. For example an additional labelled particle (same or different label) with antibodies against a component of the primary labelled particle could be used (e.g. an immunogen coupled to the labelled particle to which good antibodies exist). Once again a magnetic holding and wash step would be performed to remove any unbound secondary label coated labelled particles. The reader would then measure the label in the same manner (if the same label was used) or in a different manner if a different label was used. This additional measurement could be used to increase the range and sensitivity of the measurement.

Many current POC immunoassays that use fluorescent labels measure the labels in a blood or plasma matrix. As previously described there are many components in blood and plasma (human serum albumin, bilirubin, haemoglobin etc) that interfere with either the excitation or emission wavelength used to measure the concentration of the captured fluorophore. As a result the precision within and between bloods of other POC immunoassays can be affected purely by the measurement of the fluorescent label alone (in addition to all the matrix binding problems). As a result fluorophores are used that try to minimise these effects, these are therefore not necessarily the best fluorescent label to use but a necessity of making the fluorescent measurement in a "dirty matrix". The present platform will however, allow an extended choice of fluorescent labels allowing the labels that result in the best assay performance to be chosen. This alone is an advantage; it also means multiplexing can more easily be achieved as discussed.

The present invention makes the possibility of multiplexing (i.e. the detection of more than one analyte using a single sample) within a single channel using magnetic particles as a capture phase possible. For example, if it is not possible to use multiple fluorescent labels due to the optical properties of blood and plasma then multiplexing would not be possible within a channel because there is no way to provide specificity of measurement as the magnetic particles cannot be spatially distributed into magnetic particles specific for analyte 1, 2 etc. This is why planar capture is used as capture phase in POC platforms that can perform multiplexing. For example, some panel tests use the same fluorescent label (due to the blood and plasma limitations) for the labels with the capture antibodies for each analyte spatially distributed on the strip to allow multiplexing capability. As the magnetic particles are mobile and susceptible to the applied magnetic field, specificity due to spatial distribution of the magnetic particles (specific against different analytes) is difficult to achieve due to the fluorescent label optical limitations in plasma or blood. However, by providing a wash step as in the present invention, multiplexing within a single channel using magnetic particles' and fluorescent labels become a reality. In addition the 6 channel strip design allows multiplexing to be achieved with one fluorophore and thus increase the overall multiplexing capability when within channel multiplexing (multiple fluorophores) is taken into account.

Due to the flexibility offered by the ability to perform one step, multi-step assays and multiple wash steps there is a great opportunity to extend analyte measurement ranges or linearise the dose response curve of an assay. For example, typical immunoassay dose response curves are sigmoidal. This is driven by either reagent saturation (insufficient reagent to maintain linear binding) or saturation of the label/detection method (i.e. the detection methods becomes saturated and can no longer measure the label in a linear fashion). The present platform will however, allow a full linear response across the measurement range, and this can be achieved by several methods. For example, the reader can measure the concentration of the fluorescent particles at each stage of the multi step assay. Therefore after the initial fluorescent particle binding step has occurred, the reader could measure the fluorescence intensity. This could be a range measurement, for example, so if the intensity is over a threshold value (set during calibration) it uses the fluorescence intensity to calculate the analyte concentration (calibration 1) and the test stops at this point. If the fluorescence intensity is however below the threshold value this would indicate a low analyte concentration and the previously described additional amplification steps would occur (calibration 2) and the subsequent fluorescence intensity used to calculate the analyte concentration. This could also be achieved by using the two channels whereby one channel is tuned to make very sensitive measurements whilst the other is tuned (reagent concentration and/or binding time) to make linear measurements across the remaining portion of the analyte measurement range. Optical saturation resulting in non linearity can also be combated by reader. The present platform allows many different ways of achieving linear responses across the measurable ranges, which will allow more accurate calibration resulting in better within and between blood precision resulting in better ATE. It is envisaged that magnetic particle distribution could be used to affect both the measurement of the fluorescent label and the binding reactions. For example, the magnetic particles could be measured as a homogenous/distributed distribution throughout the channel allowing range measurements whilst the same magnetic particles could then be accumulated to increase the fluorescence intensity to drive the sensitivity of the measurement. Likewise the same principle could be used to affect the binding reactions and tune the assays accordingly.

In the cartridge design shown in FIG. 1, two identical channels are shown; however, measurements do not require this, therefore one channel in the cartridge may be employed, and this could allow a sub 1 μL immunoassay measurement.

In comparison to the 2 channel strip design, the channels within the 6 channel strip design (shown in FIG. 11) are joined. In the 2 channel strip the two channels are separate entities that are not joined. The 6 channel strip design can have joined channels (as can the 2 channel strip design) because the system is a sealed system. In FIG. 11, electrodes are shown that could be used for electrochemical measurements (219) that could be situated in one or more of the sample channels. Electrodes are also shown that could be used for electrochemical and/or detection of sample fluid as well as acting as fluidic stop features (220, 221). FIG. 11 also shows 2 alternative strip design features that would lend the strip to be filled with the test sample being presented to either the end of the strip (217) or the top of the strip (218). Each test channel within the test cartridge can have one or more wash ports (206, 208, 200, 202).

The strip wash ports (200, 202) are closed (sealed by the reader). After a certain amount of time, (e.g. 5 minutes), the reader can position a magnet in contact with the test strip, or in close proximity to it, which will result in the magnetic beads being accumulated into a tight band which will be held in position during the primary wash step. The syringe pump cartridge can then be actuated in order to perform a wash step using liquid or gas, either one channel at a time, for example using valves to control the opening and closing off of each channel. (e.g., the first port (206) in isolation). Or all channels at the same time whereby each port (206 and 202) is open to the syringe pump cartridge through the absence of a valve system, or a valve system where all associated valves are open. The preferred embodiment is the case where no valves are present, neither in the reader nor the disposable test cartridge. When the blood is washed out by buffer or gas (e.g. air) being introduced through the first port (206) the blood is pushed over a fluidic stop feature (221) into the sink (210). The previously described magnetic particle accumulation, relaxation processes by permanent or electromagnets etc remains exactly the same. In the case where the syringe pump cartridge has washed the test cartridge test channels with gas for a one step assay, at this point the final fluorescent measurement for each channel can be made in the detection/measurement area (222). Note that in this case the measurement is that of an accumulated magnetic bead band—fluorophore complex in air. In the case of a multiple step assay, the reader is required to perform additional tasks as stated below.

The blood is not pushed into the other channels (212, 213, 214, 215, 216) as the ports (200, 202) are either sealed or under positive pressure/force due to the syringe pump cartridge acting on these ports at the same time. (In this case no valves are required neither in the reader nor the disposable test cartridge). Therefore the only place for the displaced blood to go is into the sink (210). Each channel has at least one fluid input port(s)s, therefore as the first port is open (e.g. 206) and being used as a port to dispense fluid into the cartridge, additional ports (e.g. 208) located up channel can be closed preventing any fluid being dispensed up the channel. The blood is therefore washed from the channel and into the sink.

A secondary delivery of label can be performed or alternatively the magnetic particle analyte complex can be transferred up the channel to the zone where the label is deposited. (211,212,213,214,215,216). Note that printed features on the strip design can be used to contain these reagents in a pre defined area. This concept could also be applied to the primary reagents deposited in the test sample channel (223). This secondary delivery of label process can again be performed individually in a channel by channel process, or be performed on all channels at once. When multiple ports are used for a channel, this process relies on the ports (200, 202, 206, 208) being opened and closed (only one port is open per channel at a time), In the case of a single port associated with each channel, this is not necessary. In the case of the delivery of the label the first strip wash port (206) used for the wash step would be closed, and the second port located up channel would then be opened and used to dispense fluid to rehydrate and deliver the label to the magnetic particle-analyte complex or remove air (resulting in a transferral event). The transferral event is possible because the strip is a sealed system, and instead of pumping fluid into the strip, air is sucked from the strip by the "pump" resulting in the magnetic particle-analyte complex in buffer being sucked along the channel to the deposited label. This process would then be repeated for the remaining channels (212, 213, 214, 215, 216).

In the case where there is only one port associated with each test channel (FIG. 26, 224), the air volume present in the area (225) between the test sample and the port can be used to displace the sample from the sample channel area (filled from the sample entry port (226)). Thus in the case of the syringe pump cartridge containing fluid, only one port is required to perform a 2 step assay, as the primary wash is performed using air that is already present in the test cartridge test channel, allowing the subsequent fluid pumped from the cartridge to rehydrate the secondary reagents (deposited in region identified by point 227) and present them to the magnetic particle complex present in the sample channel area of the test channel. It is possible to perform a 1 step assay with an air wash with only 1 port (224) associated with each channel, this is the cartridge design (MST Pro Strip V1, FIG. 26) associated with the experimental section.

As discussed previously the present platform allows multiple analytes to be measured within each channel. Multiplexing can be performed easily in one channel by depositing magnetic particles with different binding agents against the analytes to be measured. This could be achieved by making individual preparations of antibody functionalised magnetic particles and then combining them and depositing them into the sample channel. In comparison a single preparation could be made whereby a mixed antibody population (against all the analytes that are going to be measured) are coupled to a magnetic particle population resulting in magnetic particles having a number of different antibodies coupled thereto. In both embodiments, fluorescent latex particles/fluorophores preparations could be made conferring the required antibody specificity against the analytes to be measured allowing a classical immunoassay "sandwich" complex to be made (immunoassays employing fluorescent measurements in blood and plasma could not perform these measurements as magnetic particles specific to different analytes could not be spatially distributed as previously described). Further amplification steps could still be performed if needed; and the reagents could be further tuned to allow this. There is an extensive range of fluorophores available with different excitation and emission wavelengths and it is envisaged that up to 5 different analytes could be measured within one channel. In addition to the immunoassay measurements, electrochemical measurements could also be incorporated into the strip measurement. For example, an electrochemical measurement of glucose concentration and a glycosylated haemoglobin measurement could be performed using the present platform. For example, in the case of an electrochemical glucose measurement, an additional set of electrodes would be incorporated mirroring the position of the hematocrit electrodes in the other channel. All the necessary reagents would be deposited on the electrodes. As the blood fills the channels and all the previously described immunoassay events occur, the electrochemical measurement of the blood glucose occurs, the reader interprets the glucose concentration and the blood is washed out into the sink. The present platform will therefore be able to incorporate a very diverse range of measurements upon one cartridge.

Many of the current POC immunoassays platforms require refrigerated storage of the strips. The present invention may avoid such problems by employing features that make room temperature stability possible to obtain. For example other POC immunoassay systems have buffer pouches that contain an enzymatic substrate (a wet reagent), these substrates have limited room temperature stability, and as a result the product has a refrigerated stability profile. In comparison the only "wet" reagent" of the present invention is the buffer reservoir/reservoirs cartridge. This is not contained within the sample cartridge and as buffer does not generally go off at room temperature, the present invention avoids this problem. Likewise none of the reagents are wet reagents, as they will all be deposited in the cartridge and resuspended by the buffer when delivered to the sample channel or resuspended by the blood. Deposited dry reagents will thus avoid any wet reagent instability; likewise enzyme labels (i.e. enzyme-antibody labels) have been avoided (due to their poor stability profiles) and stabilisation formulations can be optimised for a single reagent (e.g. magnetic particle) without impacting the stability profile of other reagents (e.g. the label).

EXPERIMENTAL SECTION

Materials:
Maleimide-PEG2-biotin:
Thermo Scientific, Cat 21901 (EZ-link maleimide-PEG2-biotin).
Fluorescent Amine Latex Particles:
Invitrogen, Cat F8765 (1 μm yellow-green fluospheres with amine surface functionalisation)
Fluorescent Neutravidin Latex Particles:
Invitrogen, Cat F8776 (1 μm yellow-green fluospheres with neutravidin surface functionalisation)
Paramagnetic Particles:
Ademtech, Cat 03223 (200 nm Strep+ paramagnetic particles)
Antibody 1H12:
Hytest, Cat 4P33 MAb 1H12 (Anti-PSA, human)
Antibody 5A6:
Hytest, Cat 4P33 MAb 5A6 (Anti-PSA, human)
PBS:
Thermo Scientific, Cat 28372 (BupH phosphate buffered saline packs)
BSA:
Sigma, Cat A4503-50G (Albumin, from bovine serum)
Water:
Sigma, Cat W4502 (water for molecular biology)
2MEA:
Thermo Scientific, Cat 20408 (2-mercaptoethanolamine hydrochloride)
SPDP:
Pierce, Cat 21857 (N-Succinimidyl 3-(2-pyridyldithio)-propionate)
PSA:
Hytest, Cat 8P78 (prostate specific antigen)
Biotin Quantification Kit:
Thermo Scientific, Cat 28005 (Pierce biotin quantification kit)
Size Exclusion Columns:
Thermo Scientific, Cat 89882 (Zeba spin desalting columns)
Size Exclusion Columns:
GE Healthcare, Cat 17-0851-01 (PD10 columns)
EDTA:
Sigma, Cat EDS-100G (ethylenediamine tetracetic acid, anhydrous)
Tween:
Sigma P7949-100ML (Tween-20)
DMSO:
Thermo Scientific, Cat 20684 (dimethylsulfoxide)
Reagent Preparation Preparation of Paramagnetic Particles and Latex Particles Using Streptavidin-biotin and Neutravidin-biotin Interactions Respectively Antibody
Antibody Disulphide Bond Reduction for Biotinylation
Use undiluted antibody (1H12 and 5A6) stock at a concentration between 2 and 7 mg/ml. An appropriate volume of antibody stock is removed to give 1 mg antibody. An appropriate volume of 14.28 mM EDTA in PBS, pH 7.2 is added to 1 mg antibody to give an EDTA concentration of 1 mM.
6 mg of 2MEA is dissolved in 100 ul 1 mM EDTA in PBS, pH 7.2. 1 ul of this 2MEA solution is added per 10 ul of antibody solution. This solution is mixed and incubated in a waterbath at 37 deg for 90 min.

This solution is then passed through a PD10 column (pre-equilibrated with 1 mM EDTA in PBS, pH 7.2) and 500 μl fractions collected. A sample from each fraction is taken and measured on UV spectrophotometer, with the absorbance at 280 nm used to quantify the protein found in each fraction. The fractions containing significant concentrations of protein are chosen and combined and remeasured on the UV spectrophotometer. This measurement is used to determine the antibody concentration using an extinction coefficient of the antibody of 1 mg/ml=1.4 absorbance units at 280 nm.

Binding of Maleimide-PEG2-Biotin to Antibody
Maleimide-PEG2-biotin is dissolved in 1 mM EDTA in PBS, pH 7.2 to give a 20 mM solution. An appropriate volume of this is added to the reduced antibody to give a 40 times molar excess of maleimide-PEG2-biotin over reduced antibody. This is then mixed and incubated for 3 hours at room temperature.

This is then passed through another PD10 column which has been pre-equilibrated with 1 mM EDTA in PBS, pH 7.2. 500 μl fractions are collected and measured using the UV spectrophotometer at 280 nm. The fractions containing significant protein levels are chosen and combined. A sample of this solution is measured again at 280 nm by absorbance, and the concentration of antibody determined using the extinction coefficient of the antibody of 1 mg/ml=1.4 absorbance units at 280 nm. The number of biotins bound per antibody are then determined using the Pierce biotin quantification kit, according to the manufacturer's instructions.

Latex
Biotinylated Antibody 5A6 Binding to Latex
1 μm neutravidin coated latex is washed in 0.1% tween-20 in PBS, pH 7.2 (using centrifugation at 16100×g for 3.5 min, 4 deg C.) and resuspended in the same at a concentration of 0.5% solids. Biotinylated antibody 5A6 is diluted to a concentration of 200 μg/ml in 0.1% tween-20 in PBS, pH 7.2. An equal volume of 200 μg/ml b5A6 is then added to 0.5% latex. This solution is mixed well and incubated for 2 hours at room temperature with shaking on a rotary mixer (30 rpm) in the dark.

The particles are then washed 4 times (using centrifugation at 16100×g, 3.5 min at 4 deg C.) with an equal volume of PBS, pH 7.2 to remove any unbound biotinylated antibody and resuspended in PBS, pH 7.2 to give a latex concentration of 0.25% solids.

This will be referred to in the text as functionalized latex 1.

Paramagnetic Particles
Binding of Antibody to Particle
200 nm streptavidin coated paramagnetic particles are washed (using a magnetic separator) in 0.1% tween in PBS, pH 7.2 and resuspended in the same to give a concentration of 0.5% solids. Biotinylated antibody 1H12 is diluted in 0.1% tween in PBS, pH 7.2 to give 50ug/ml. An equal volume of 0.5% paramagnetic particles and 50 ug/ml biotinylated antibody are combined, mixed and allowed to incubate for 70 min at room temperature, with shaking using a rotary shaker at 30 rpm.

The paramagnetic particles were then washed 4 times (using a magnetic separator) in an equal volume of 0.1% tween in PBS, pH 7.2 and resuspended in the same to give a concentration of paramagnetic particles of 0.5% solids. This will be referred to in the text as functionalized paramagnetic particles.

Preparation of Latex Particles Using Amine-SPDP Interactions

Antibody

Antibody Disulphide Bond Reduction for Binding to SPDP

Use undiluted antibody (5A6) stock at a concentration between 2 and 7 mg/ml. An appropriate volume of antibody stock is removed to give 100 μg antibody. An appropriate volume of 14.28 mM EDTA in PBS, pH 7.2 is added to 100 μg antibody to give an EDTA concentration of 1 mM.

6 mg of 2MEA is dissolved in 625 μl 1 mM EDTA in PBS, pH 7.2. 1 ul of this 2MEA solution is added per 10 ul of antibody solution. This solution is mixed and incubated in a waterbath at 37 deg for 90 min.

This solution is then passed through a Zeba spin desalting column (pre-equilibrated with 1 mM EDTA in PBS, pH 7.2) and the flow through collected. A sample of flow through is taken and measured on UV spectrophotometer, with the absorbance at 280 nm recorded. This measurement is used to determine the antibody concentration using an extinction coefficient of the antibody of 1 mg/ml=1.4 absorbance units at 280 nm.

Latex

Amine functionalized fluorescent latex is washed in 1 mM EDTA in PBS, pH 7.2 (using centrifugation at 16100×g for 3.5 min, 4 deg C.) and resuspended in the same at a concentration of 0.5% solids.

SPDP is dissolved in an appropriate volume of DMSO to give 20 mM concentration SPDP. SPDP in DMSO is then added to the 0.5% latex to give 1 mM SPDP. This is mixed and incubated in the dark for 70 min with gentle shaking (30 rpm on rotary mixer). The latex is then washed 3 times with 2× reaction volume of 1 mM EDTA in PBS, pH 7.2 (using centrifugation at 16100×g for 3.5 min, 4 deg C.). The latex is then resuspended in the same in the appropriate volume to give a latex concentration of 0.5% solids. This gives latex that is bound to SPDP, ready for attachment of reduced antibody.

Binding of Reduced Antibody Latex with Bound SPDP

Reduced antibody 5A6 is diluted to 1 mg/ml in 1 mM EDTA in PBS, pH 7.2. 1 mg/ml antibody is then mixed with 0.5% latex bound to SPDP in a 1:1 ratio. This gives a binding mixture of 0.25% latex with 500 μg/ml antibody in 1 mM EDTA in PBS, pH 7.2.

This binding reaction is incubated at room temperature in the dark for 19.5 hours and then washed 4 times with 1× reaction volume of PBS, pH 7.2 (using centrifugation at 16100×g for 3.5 min, 4 deg C.). The latex was then resuspended in PBS, pH 7.2 in the appropriate volume to give 0.25% solids.

This will be referred to in the text as functionalized latex 2.

Assay Procedures

Assay 1: 1 Step Wet Assay with Manual Wash

7 μl 0.5% functionalized paramagnetic particles (with bound b1H12) is added to an eppendorf and placed on a magnetic separator. The supernatant is removed and the particles resuspended in 49 μl 30 mg/ml BSA in 0.05% tween-20 in PBS, pH 7.2. To this, 7 μl 0.25% functionalized latex 1 (with biotinylated 5A6 bound) is added and the solution mixed.

8 μl of this mixture is removed and added to 2 μl PSA protein in 60 mg/ml BSA in PBS, pH 7.2 (N.B. PSA is at 5× required final concentration). This is mixed and incubated for 5 min at room temperature.

The eppendorf is then added to a magnetic separator and the supernatant carefully removed. 20 μl 0.05% tween-20 in PBS, pH 7.2 is then added to the pellet, whilst remaining on the magnetic separator. The supernatant is removed and a fresh 20 μl 0.05% tween-20 in PBS, pH 7.2 used to resuspend the particle complexes, once removed from the magnetic separator.

This is repeated with several different concentrations of PSA, producing washed wet assay complexes which have been diluted 2× from the original reaction.

These diluted, washed complexes are measured in 3 different ways as follows:

Washed wet assay measurement 1:

2 μl washed wet assay complexes are added to 38 μl PBS in a 384 well black Optiplate for fluorescent measurement. The plate is then measured using a Perkin Elmer Victor3 V. The fluorescent signal in the well is measured using the inbuilt program 'Fluorescein (485 nm/535 nm, 0.1 s)', adapted for use in a 384 well format. This program uses excitation at 485 nm and emission at 535 nm with a 0.1 s measurement time.

Figure 12:
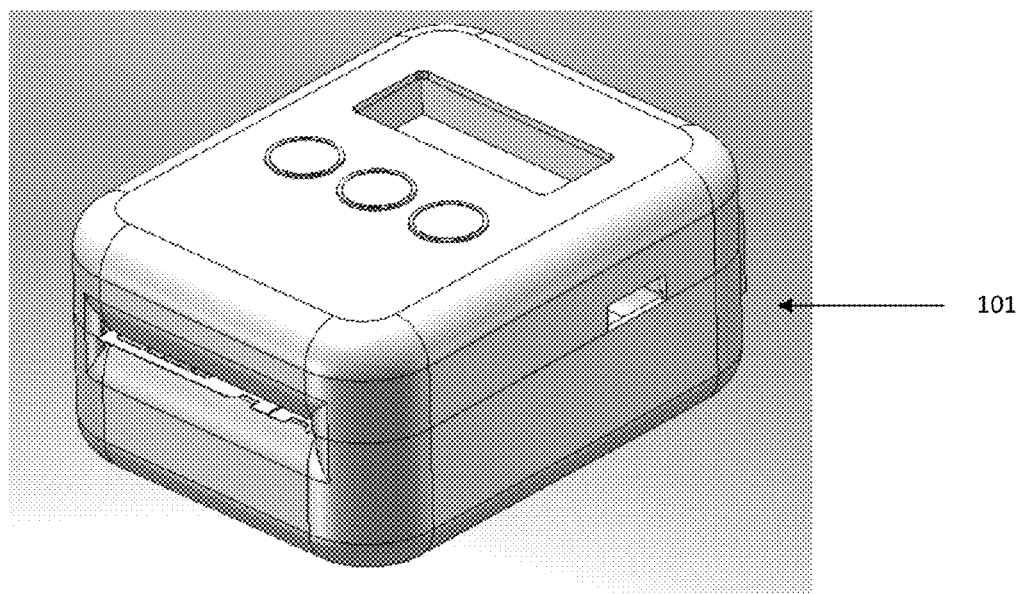
FIG. 12 is a schematic of a reader device in accordance with the present invention.
Figure 12:
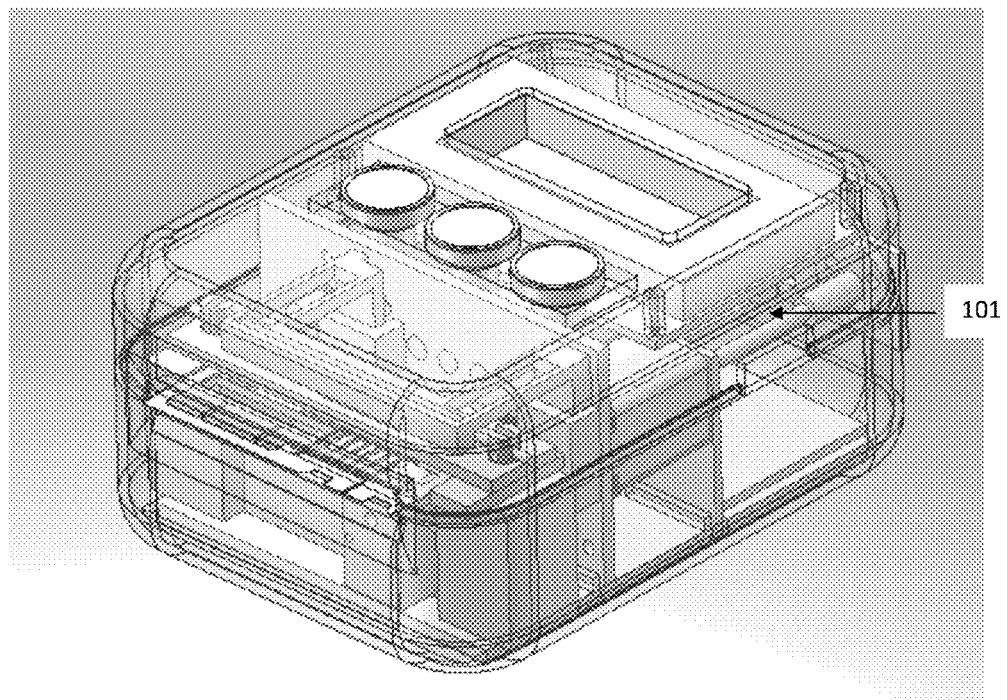
Figure 13:
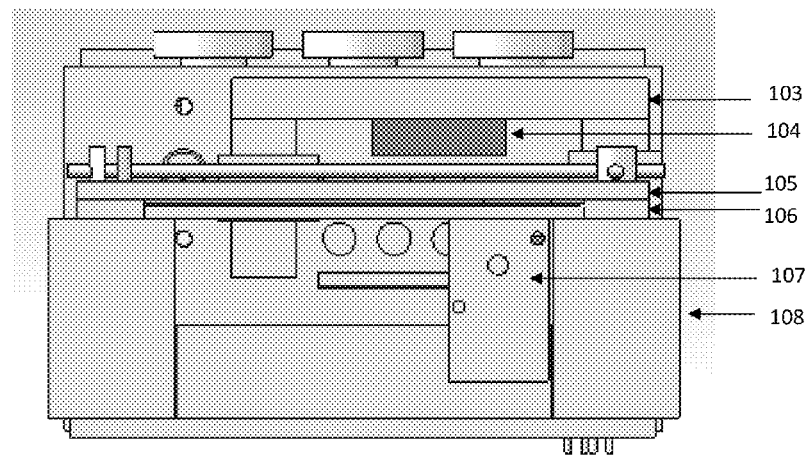
FIG. 13 is a schematic of the internal mechanisms associated with a reader device in accordance with the present invention
Figure 13:
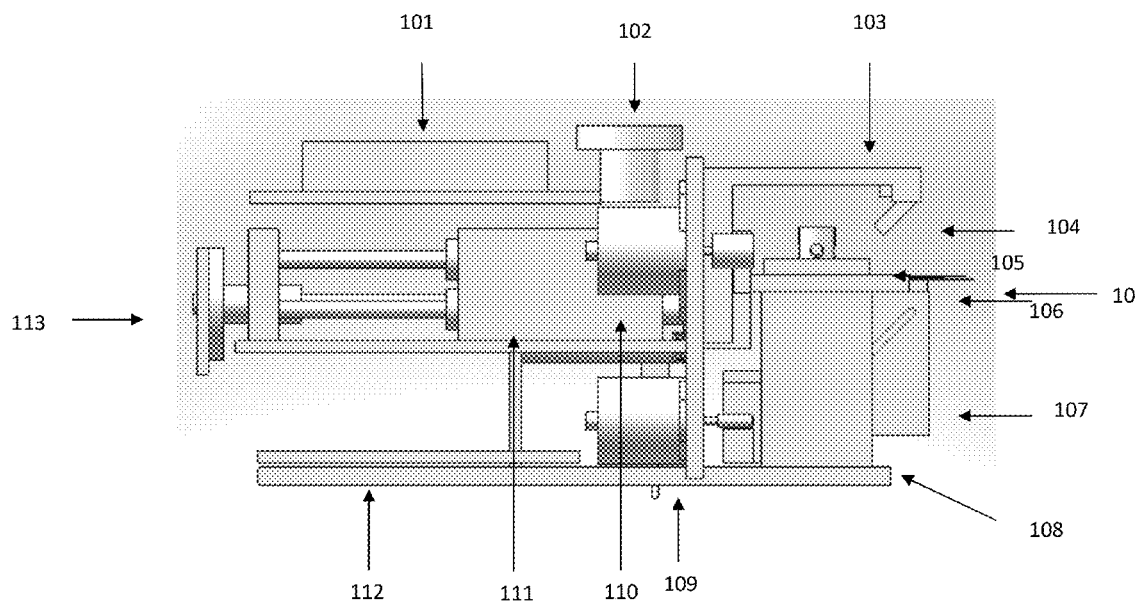

Washed wet assay measurement 2:

8 μl washed wet assay complexes are used to fill a 'MST pro strip V1' cartridge (as shown in FIG. 26). The washed wet assay reagents were applied to the cartridge via sample inlet port (226). This allowed the sample (in this case washed wet assay reagents) to fill the 6 channels up to fluidic stop features (229, 228, 239, 237) (which can also act as fill detect electrodes via electrical connection to the reader through connector (230). This cartridge is inserted into a 'MST pro meter V1' reader (as shown in FIG. 12) and the signal measured by the optics in the reader which scans each channel using a linear movement of the optical head at position (222, 242) In this method, the washed wet assay complexes are spread homogeneously throughout the channel and hence detection area (i.e. they are not concentrated into a band by use of a magnetic field). (It should be noted that measurements are not made in channel (243) in these experiments as this has been set up as an hematocrit correction channel with hematocrit electrodes (237) for whole blood measurements which are not used here. It should also be noted that the hematocrit electrodes, have in this case been made from a hydrophobic material to prevent filling of the entire channel and hence waste sample. For functioning hematocrit electrodes an less hydrophobic or hydrophilic material would be used.)

Washed wet assay measurement 3:

The cartridges (MST pro strip V1) filled with washed wet assay complexes, as described in washed wet assay measurement 2 above were then remeasured using the Victor3 V. This was carried out by attaching the cartridge to a 384 well black Optiplate and aligning the cartridge channel to be measured (at position 222, 241) over a specific well. The fluorescent signal of the channel was then measured by measuring the signal of the appropriate corresponding well using the inbuilt program 'Fluorescein (485 nm/535 nm, 0.1 s)', adapted for use in a 384 well format. This program uses excitation at 485 nm and emission at 535 nm with a 0.1 s measurement time. This was repeated for each channel to be measured.

Figure 16:
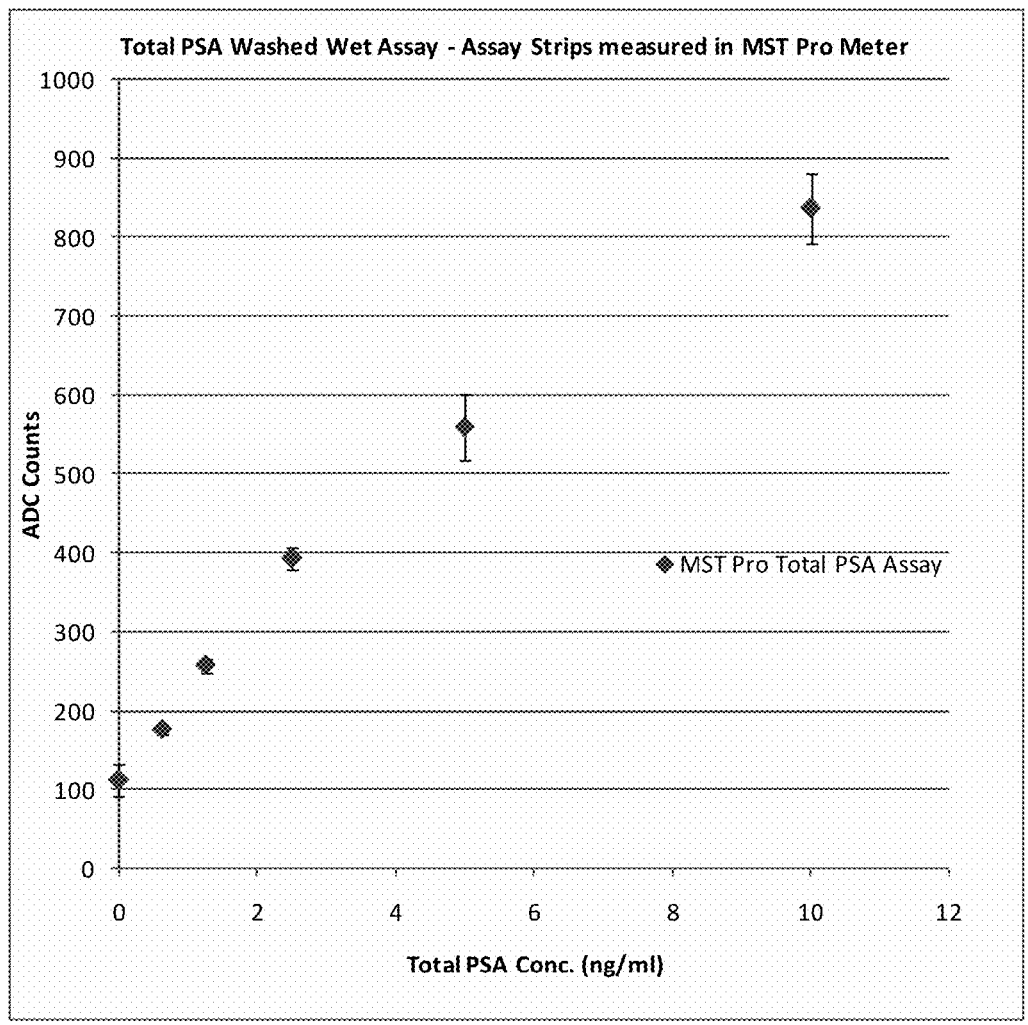
FIG. 16 shows graphed experimental results of a total PSA washed wet assay with the assay cartridges measured in the MST Pro Meter V1 in accordance with the current invention.
Figure 17:
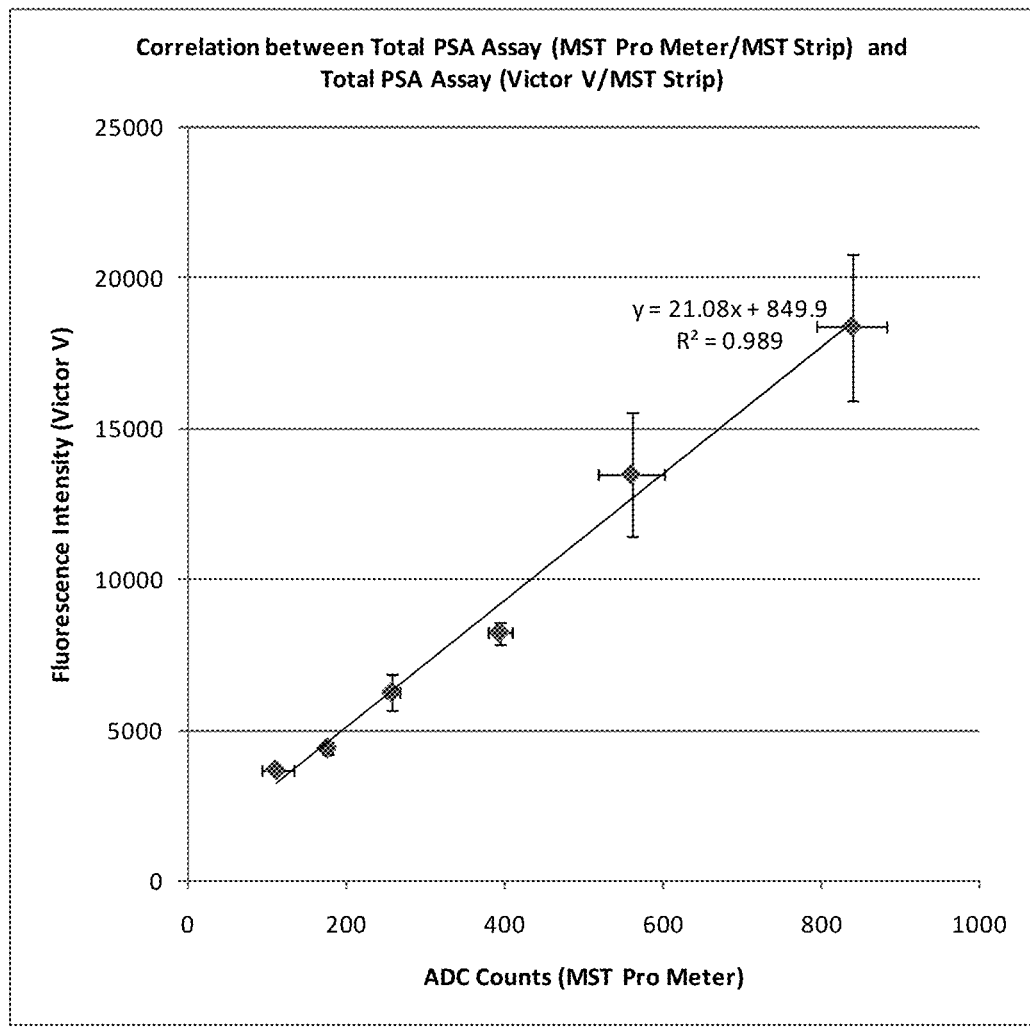
FIG. 17 shows graphed experimental results showing the correlation between the Total PSA washed wet assays measured in strips in the MST Pro meter and the Victor V reference instrument.
Figure 18:
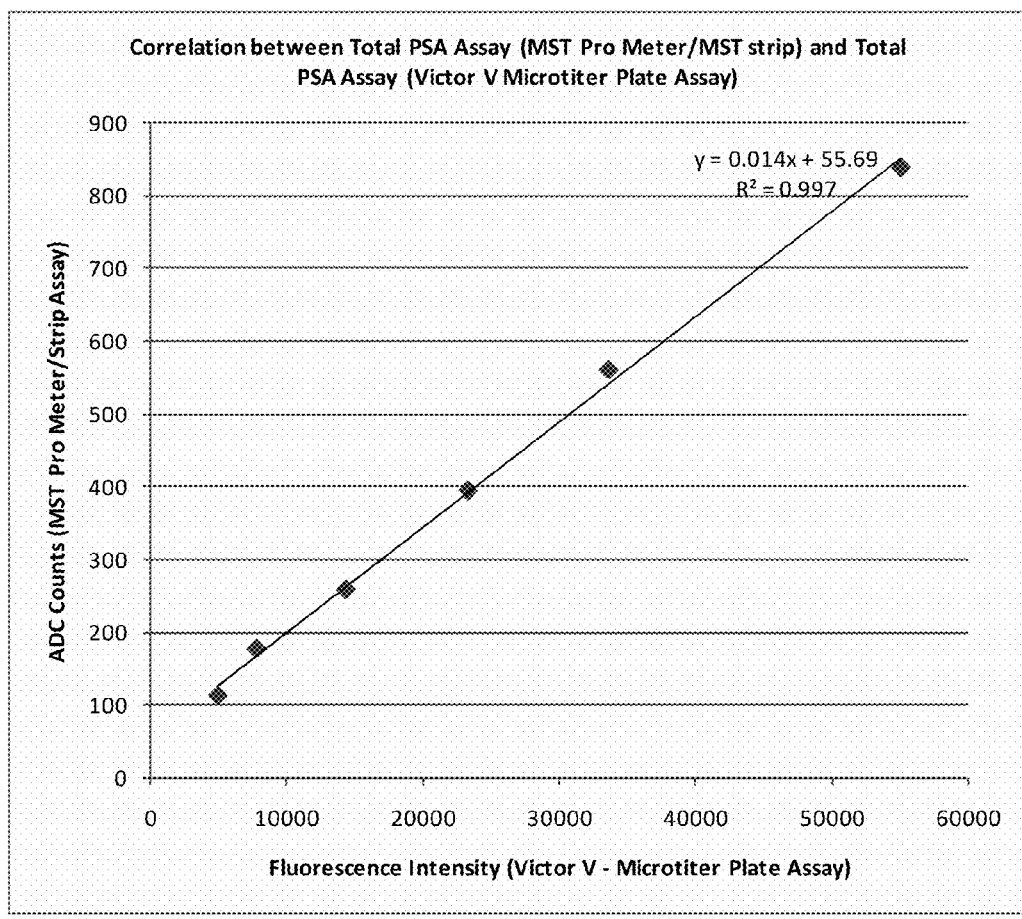
FIG. 18 shows graphed experimental results showing the correlation between the Total PSA washed wet assays measured in strips in the MST Pro meter and the Victor V reference instrument.

Results for Assay 1:

Results for comparisons between the different measurement methods of the washed wet assay complexes are shown in FIGS. 16, 17 and 18.

FIG. 16 shows the total PSA washed wet assays measured in a MST pro strip V1 in the MST Pro Meter V1 (washed wet assay measurement 2). Total PSA wet assays were performed as per the experimental methodology described above. The total PSA washed wet assay was measured in the MST Pro Meter V1 as shown in FIG. 12. The results clearly show a systematic assay response with an initial linear phase followed by a non linear phase. The clinical cut off for Total PSA assays used in the screening of prostate cancer is 4 ng/ml. The assay is clearly sensitive enough to make accurate measurements above the below the cut off threshold value in a quantitative manor. In this data set the paramagnetic particle-PSA-latex bound complexes are homogenously distributed throughout the strip channels during the optical measurement phase. The MST Pro Meter has only been utilised to measure Total PSA washed wets assays in a strip.

FIG. 17 shows the Correlation between the Total PSA washed wet assays measured in strips in the MST Pro meter and the Victor3 V. The same strips (containing the washed Total PSA washed wet assays) that were measured in the MST Pro Meter (see FIG. 16, wet washed assay measurement 2) were then measured in the Victor3 V (washed wet assay measurement 3), with the results are summarised in FIG. 17. A clear correlation between the two measurement methods (MST Pro Meter V1 and the Victor3 V) is observed especially considering the Victor3 V is a conventionally plate reader and is not intended to measure fluorescent signals in laminate strip. This probably explains the greater error associated with the Victor V measurements. The data demonstrates the optical measurement performed by the MST Pro Meter V1 is a highly sensitive accurate measurement especially when compared to a very expensive "gold standard" fluorescent plate reader technology (Victor3 V).

FIG. 18 shows the correlation between the Total PSA washed wet assays measured in strips in the MST Pro meter and the Victor V. The Total PSA washed wet assays were also measured in a conventional microtiter plate assay using the Victor3 V (washed wet assay measurement 1). These results were then compared to the Total PSA washed wet assays measured in a strip using the MST Pro Meter V1 (washed wet assay measurement 2). The correlation between the two measurement methodologies is shown in FIG. 18. An excellent correlation is observed between the two methodologies demonstrating the ability to make highly sensitive and accurate measurements using the MST Pro Meter and Strip (Platform) in very small sample volumes. The sample channel is 1 µL however the volume measured in the MST pro strip V1 by the optical block is only approximately 0.2 µL.

Assay 2: 1 Step Wet Assay with Wash and Measurement Carried Out in 'MST Pro Meter V1' Reader Assay reagents are combined in the following volumes and concentrations into an eppendorf tube:
0.5% functionalized paramagnetic particles (with bound b1H12): 1 µl
30 mg/ml BSA, 0.05% tween all in PBS, pH 7.2: 6 µl
0.25% functionalized latex 1 (with biotinylated 5A6 bound): 1 µl
PSA (diluted in 60 mg/ml BSA in PBS, pH 7.2): 2 µl All reagents are mixed and then used to fill the channels of a 'MST pro strip V1' cartridge (see FIG. 26 for description of cartridge used) via sample inlet port (226) where it fills the channels up to the fluidic stop features (229, 228, 237). This cartridge is inserted into a 'MST pro meter V1' reader (see FIG. 12 for a description of the reader used) via connector (230), where a 5 min incubation occurs. The reader then brings a permanent magnet to the cartridge where it acts to collect the paramagnetic particles and anything bound to them into the detection area (222, 241). The optical reader head then carries out a measurement of the fluorescent signal by scanning across the detection areas of each channel (222, 241). This measurement includes the fluorescent latex specifically bound to the paramagnetic particles via PSA and also any unbound fluorescent latex which is found within the detection area (see FIG. 20 for description of these results). The sealing head of the reader makes a fluid tight seal with input ports of channels 1,2,3, 4,5,6 (224, 231, 232, 233, 234, 235 respectively). Whilst the paramagnetic complexes are maintained in place by the magnet, the reader carries out a wash step by expelling either a) wash buffer (0.1% tween-20 in PBS, pH 7.2) or b) air from the syringe pump cartridge (as shown in FIG. 15, bottom image of 6 chamber syringe cartridge) via the input ports (231, 232, 233, 234, 235, 224) to displace the sample fluid from the channel, and hence remove the unbound latex from the detection area, where it is displaced into the sink (236). The optical reader head then carries out a measurement of the remaining fluorescent signal from the binding complexes within the matrix of the wash substance (fluid or air) by scanning across the detection areas of each channel (222, 241) (see FIG. 19 for a description of these results using the air wash and FIG. 21 for results using the wash buffer wash).

Figure 20:
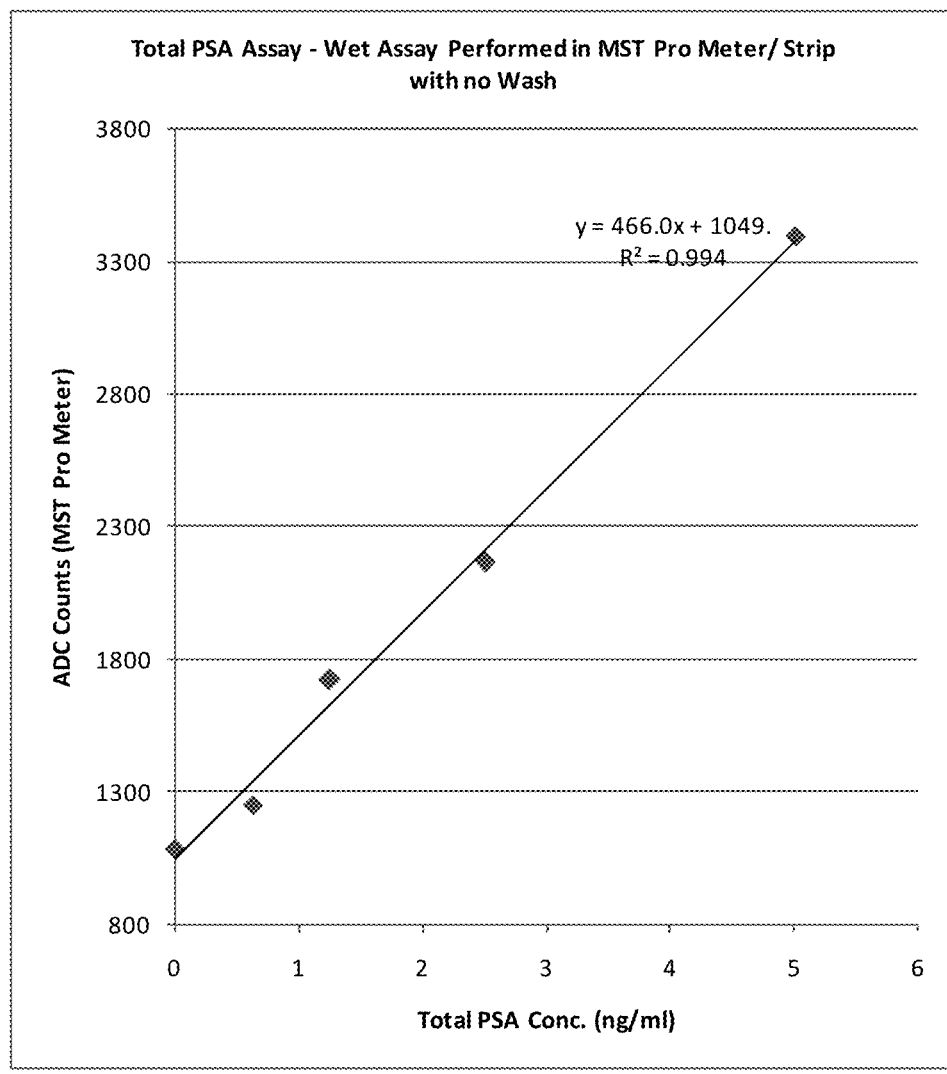
FIG. 20 shows graphed experimental results showing the total PSA wet assay performed in the MST Pro Meter and Strip, does not use a wash step and measures the fluorescence intensity of the fluorophore after the magnetic particle-PSA-fluorescent latex complex are accumulated by the magnet.

Results for Assay 2:

FIG. 20 shows a Total PSA wet assay performed in the MST Pro Meter and Strip, does not use a wash step and measures the fluorescence intensity of the fluorophore after the paramagnetic particle-PSA-fluorescent latex complex are accumulated by the magnet. A highly effective integrated onboard control is summarised in FIG. 20. Before an air or fluid wash is performed by the meter the paramagnetic particle-PSA-fluorescent latex particle complexes are accumulated by the magnet. At this point the meter can perform an optical read of the channels and quantify the concentration of fluorescent latex label as shown in FIG. 20. Interestingly the fluorescent response ADC counts is related to PSA concentration, i.e. a dose response without a wash step, which could be used as a independent homogenous assay. The meter then performs the wash step and measures the concentration of the paramagnetic particle-PSA-fluorescent latex complexes. The assay fluorescent signal should always be lower after the wash step (air or fluid) as the unbound fluorescent label is removed from the channel.

Figure 19:
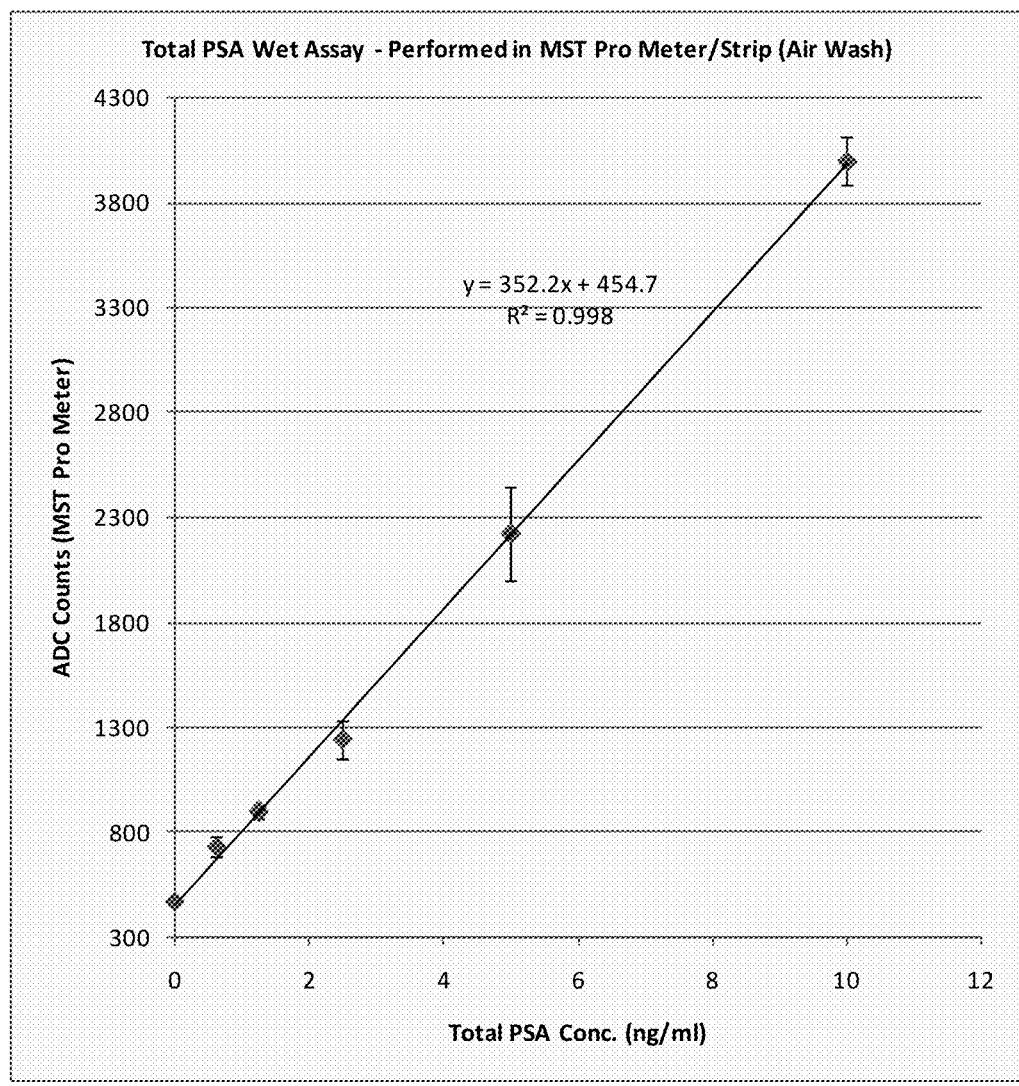
FIG. 19 shows graphed experimental results showing the total PSA wet assay performed in the MST Pro Meter and Strip, the meter using a air wash step to expel unbound label from the channel.

FIG. 19 shows Total PSA wet assay performed in the MST Pro Meter and Strip, the meter using an air wash step to expel unbound label from the channel. Total PSA washed wet assays were performed with the MST Pro Meter V1 and Strip. The MST Pro Meter V1 uses an air wash to expel the sample (containing unbound label) from the strip channels in the sink. The results are summarised in FIG. 19, the assay dose response curve clearly demonstrates a rapid, sensitive, accurate and quantitative assay response for Total PSA. The 5 minute test time would be a significant improvement on current rapid POC PSA tests, as would the improvements in sensitivity/accuracy and the quantitative nature of the assay demonstrated. Interestingly the data clearly demonstrates a "air wash" is a very effective method to remove unbound fluorescent label from the channel and that accurate sensitive measurements of the fluorescent labels bound to the paramagnetic particles via analyte (PSA) can be performed in a non liquid environment. This allows simple but highly functional assays to be formatted on the MST Pro Platform.

Figure 21:
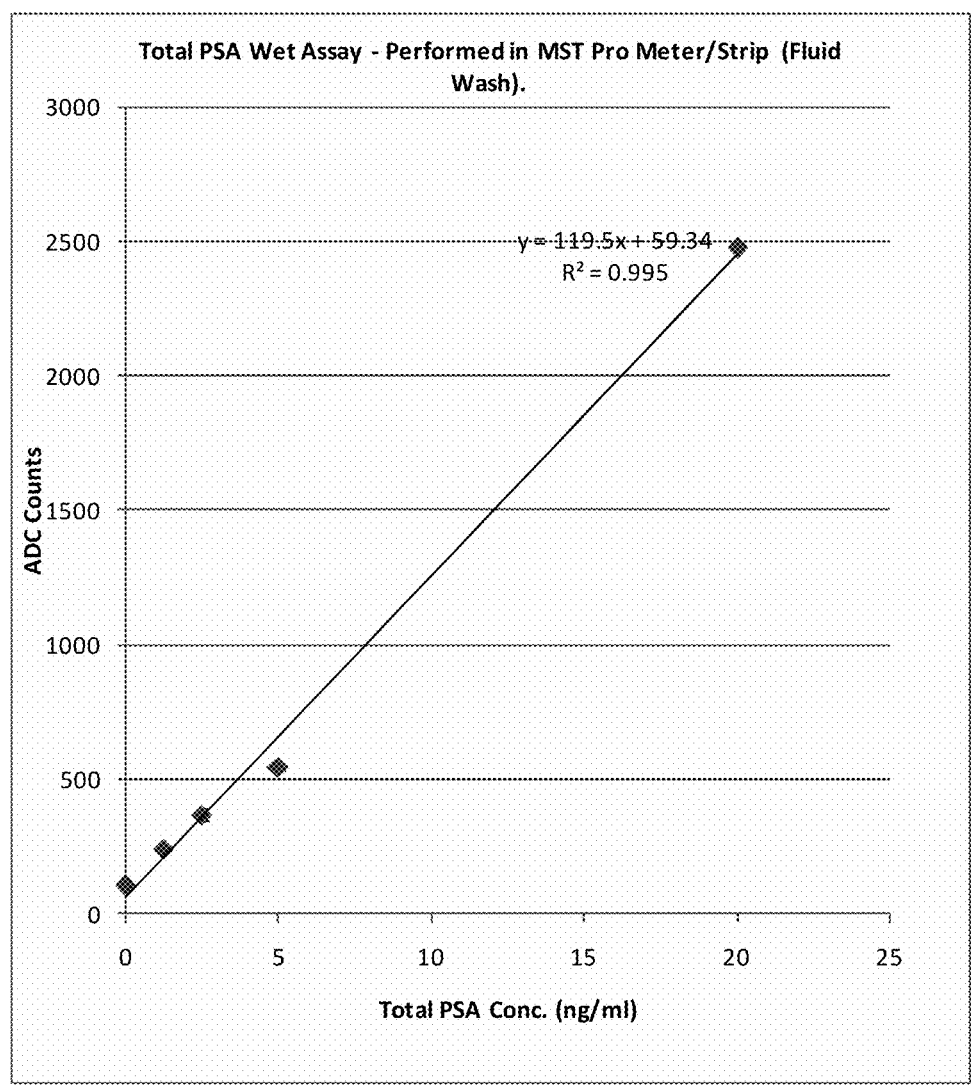
FIG. 21 shows graphed experimental results showing the total PSA washed wet assay performed with the MST Pro Meter V1 and Strip. For the data, the MST Pro Meter V1 uses a fluid wash to expel the sample (containing unbound label) from the strip channels into the sink.

FIG. 21 shows an example data dose response curve for Total PSA wet assay performed in the MST Pro Meter and Strip, where the meter uses a fluid wash step to expel unbound label from the channel. The fluid wash is highly effective demonstrating a sensitive, accurate rapid PSA test. In comparison to the air wash methodology the paramagnetic particle-PSA-fluorescent latex label complexes are optically measured in the fluid environment. The fluid buffer wash could contain components that could enhance the fluorescent signal further (for example, chelating agents, fluorescent dye release agents etc).

Assay 3: 1 Step Dry Assay with Wash and Measurement Carried Out in 'MST Pro Meter V1' Reader Reagents are deposited and dried within a 'MST pro strip V1' cartridge as follows:
8 µl 0.5% functionalized paramagnetic particles (with bound biotinylated 1H12)
8 µl 25 mg/ml trehalose in PBS, pH 7.2
8 µl 300 mg/ml BSA in PBS, pH 7.2
8 µl 0.1% tween-20 in PBS, pH 7.2
8 µl 0.25% functionalized latex 2 (with 5A6 bound via SPDP)

The above reagents are combined and 1 µl of this 1 step deposition mix added per channel of a 'MST pro strip V1' cartridge (as shown in FIG. 26). Reagents are deposited at position (223, 242) in each channel and not allowed to enter the detection area (222, 241) (this is achieved by use of a hydrophobic pen line to define the reagent deposition area on a single surface of the laminate cartridge, which is sufficient to prevent reagent spread but not strong enough to prevent sample filling of the fully assembled cartridge by capillary force). For deposition, the cartridge is half assembled, with only the bottom and middle layer of cartridge bonded together. The reagents are pipetted into the reagent deposition zone of the half assembled test sample channel (see FIG. 26, with reagent deposition zone indicated on the cartridge as point 223, 242). These are dried in an oven at 33 deg C. for 10 min. The top layer of the cartridge is then bonded to the half assembled cartridge to produce a fully assembled three layer cartridge (see FIG. 2 for an example of how the three layers come together to form an assembled cartridge, for a different cartridge design) with dried reagents. FIG. 26 (240) indicates the shape of the double sided adhesive material which is cut away to form channels and sink structures when bonded between two layers of laminate material. The cartridge is then stored in a sealed foil pouch containing desiccant until use.

PSA protein is diluted to the required concentration in 60 mg/ml BSA in PBS, pH 7.2. A cartridge containing dried reagents is inserted into the 'MST pro meter V1' reader and 8 µl PSA is then added to the cartridge to fill the test sample channels. The sample is applied to the cartridge via sample inlet port (226) and fills the channels by capillary force up to the hydrophobic fluidic stop features (229, 228, 239, 237). 5 min binding incubation occurs before the reader brings a permanent magnet to the cartridge where it acts to collect the paramagnetic particles and anything bound to them into the detection area (222, 241). The sealing head of the reader makes a fluid tight seal with input ports of channels 1,2,3, 4,5,6 (224, 231, 232, 233, 234, 235 respectively). Whilst the paramagnetic complexes are maintained in place by the magnet, the reader carries out a wash step by expelling air from the syringe pump cartridge (as shown in FIG. 15, bottom image of 6 chamber syringe cartridge) to displace the sample fluid from the channel, and hence remove the unbound latex from the detection area and displace it into the sink (236). The optical reader head then carries out a measurement of the remaining fluorescent signal (from the specific sandwich binding complexes of paramagnetic particles-PSA-fluorescent particles) which remain in air by scanning across the detection areas of each channel (222, 241) (see FIG. 22 for a description of these results).

Figure 22:
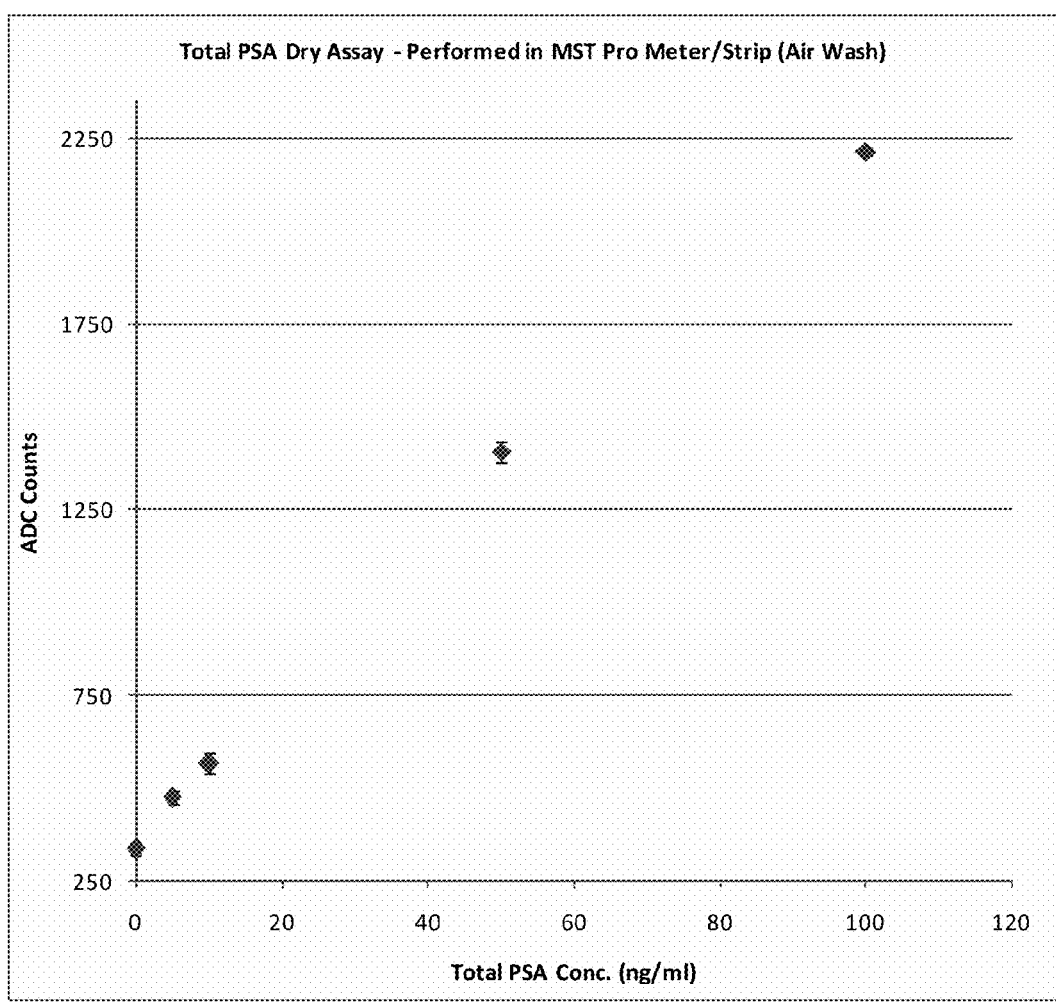
FIG. 22 shows graphed experimental results of a total PSA dry assay performed with reagents dried in the MST Pro Strip V1 and the assay performed on MST Pro Meter V1 in accordance with the current invention; 1

Results for Assay 3:

FIG. 22 shows results for a Total PSA Dry assay performed in the MST Pro Meter and Strip, the meter uses air wash step to expel unbound label from the channel. All the reagents were deposited in the strip. The dynamic range of the Total PSA assay was increased significantly by using a different fluorescent latex label preparation and by reducing the input voltage to the optical detector. The summary results are shown in FIG. 22 where the assay is a full dry assay with all reagents deposited within the strip. The assay range has been extended significantly, the linear response has been increased by 10 times (10 to 100 ng/ml), and this is of great value as some assays require assays with a low limit of detection but a large dynamic range. With such assays linearity is not maintained across the large dynamic range, resulting in reduced assay performance at higher concentrations. The MST Pro platform can overcome this limitation in several ways. For example, non linearity due to optical detector saturation can be overcome by reducing the sensitivity of the optical detector by reducing the input voltage. Therefore if binding is linear, the reduced sensitivity of the optical detector will allow the dynamic range of the assay to be increased further (the meter would contain a PSA calibration curve for the high and low optical detector setting). In comparison, if the non linearity is due to a reagent limitation, two channels of the MST Pro strip could be used to maximize assay performance across the assay range. Reagents developed to make very sensitive measurements that have a limited dynamic range could be deposited in one channel whilst reagents that are less sensitive but allow the dynamic range of the assay to be increased significantly could be deposited in another channel. Each set of reagents/channel would have its own calibration curve therefore allowing improving assay performance over whole range of the assay.

Assay 4: 2 Step Half Dry Assay (Dried Latex Particles) with Wash and Measurement Carried Out in 'MST Pro Meter V1' Reader Reagents are deposited and dried within a 'MST pro strip V1' cartridge as follows:
10 µl 0.25% functionalized latex 1 (with biotinylated 5A6 bound)
10 µl 25 mg/ml trehalose in PBS, pH 7.2
20 µl 300 mg/ml BSA in PBS, pH 7.2
10 µl 0.1% tween-20 in PBS, pH 7.2

The above reagents are combined and 1 µl of this deposition mix added per channel of a 'MST pro strip V1' cartridge (as shown in FIG. 26). Reagents are deposited at position (223, 242) in each channel and not allowed to enter the detection area (222, 241) (this is achieved by use of a hydrophobic pen line to define the reagent deposition area on a single surface of the laminate cartridge, which is sufficient to prevent reagent spread but not strong enough to prevent sample filling of the fully assembled cartridge). For deposition, the cartridge is half assembled, with only the bottom and middle layer of cartridge bonded together. The reagents are pipetted into the reagent deposition zone of the half assembled test sample channel (see FIG. 26, with reagent deposition zone indicated on the cartridge as point 223, 242). These are dried in an oven at 33 deg C. for 10 min. The top layer of the cartridge is then bonded to the half assembled cartridge to produce a fully assembled three layer cartridge (see FIG. 2 for an example of how the three layers come together to form an assembled cartridge, for a different cartridge design) with dried reagents. FIG. 26 (240) indicates the shape of the double sided adhesive material which is cut away to form channels and sink structures when bonded between two layers of laminate material. The cartridge is then stored in a sealed foil pouch containing desiccant until use.

In this 2 step assay, the first binding step (functionalized paramagnetic particles with PSA) is carried out in a wet format, before the second binding step (functionalized paramagnetic particles-PSA with functionalized latex 1) occurs using dried functionalized latex 1 within the 'MST pro strip V1' cartridge as follows:

Step1

The following reagents are combined:

2 µl 0.5% functionalized paramagnetic particles (with bound biotinylated 1H12)
6 µl 30 mg/ml BSA in PBS, pH 7.
2 µl PSA (diluted in 60 mg/ml BSA in PBS, pH 7.2)

This first step binding reaction is incubated for 5 min at room temperature before 8 µl is added to the cartridge containing dried functionalized latex to fill the test sample channels as shown in FIG. 26. The sample is applied to sample inlet port (226) where it fills the channels up to the fluidic stop features (228, 239, 229) (which are made of hydrophobic ink). 5 min binding incubation occurs before the reader brings a permanent magnet to the cartridge where it acts to collect the paramagnetic particles and anything bound to them into the detection area. The sealing head of the reader then makes a fluid tight seal with input ports of channels 1,2,3,4,5,6 (224, 231, 232, 233, 234, 235 respectively). Whilst the paramagnetic complexes are maintained in place by the magnet, the reader carries out a wash step by expelling air from the syringe pump cartridge to displace the sample fluid from the channel, and hence remove the unbound latex from the detection area (222, 241) and displace it into the sink (236). The optical reader head then carries out a measurement of the remaining fluorescent signal (from the specific sandwich binding complexes of paramagnetic particles-PSA-fluorescent particles) which remain in air by scanning across the detection areas of each channel (see FIG. 23 for a description of these results).

Figure 23:
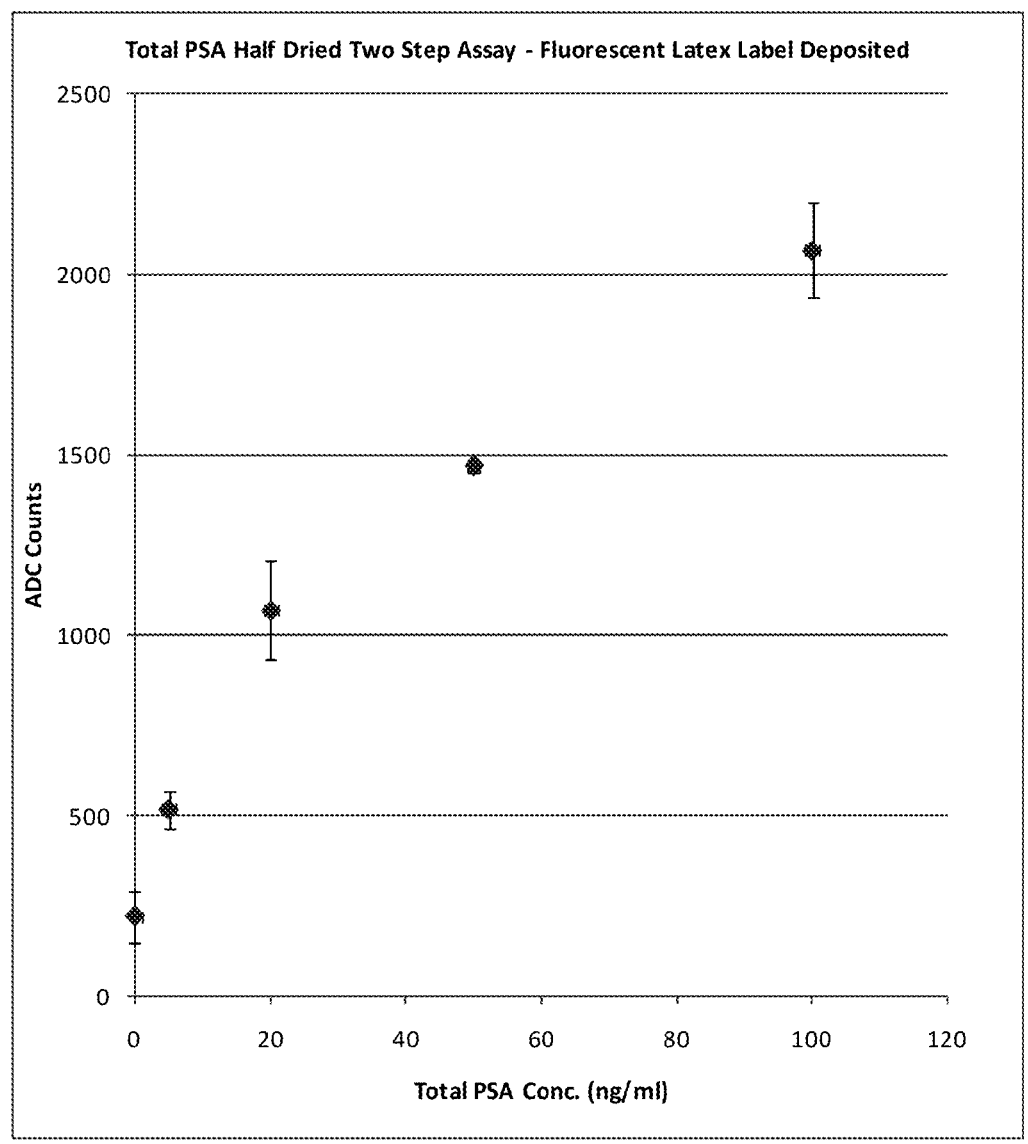
FIG. 23 shows graphed experimental results of a total PSA half dried 2 step assay performed with reagents dried in the MST Pro Strip V1 and the assay performed on the MST Pro Meter V1. In this case the fluorescent latex was deposited in the test cartridge in dry format.

Results for Assay 4:

FIG. 23 shows a Total PSA two step assay performed in the MST Pro Meter and Strip. The meter uses an air wash step to expel unbound label from the channel. Fluorescent latex label was deposited in the strip. The summary results are shown in FIG. 23. The fluorescent latex label was deposited in the strip and the sample containing PSA and paramagnetic particles was added to the strip. The meter performed an air wash and optically measured the concentration of captured fluorescent latex label. Systematic dose response curves are observed and demonstrate that two or three step assays can be formatted on the MST Pro Platform and that fluorescent latex label could be deposited in one strip and used to perform two step assays.

Assay 5: 2 Step Half Dry Assay (Dried Paramagnetic Particles) with Wash and Measurement Carried Out in 'MST Pro Meter V1' Reader Reagents are deposited and dried within a 'MST pro strip V1' cartridge as follows:

10 µl 0.5% functionalized paramagnetic particles (with biotinylated 1H12 bound)
10 µl PBS, pH 7.2
10 µl 25 mg/ml trehalose in PBS, pH 7.2
10 µl 300 mg/ml BSA in PBS, pH 7.2
10 µl 0.1% tween-20 in PBS, pH 7.2

The above reagents are combined and 1 µl of this deposition mix added per channel of a 'MST pro strip V1' cartridge (as shown in FIG. 26). Reagents are deposited at position (223, 242) in each channel (however it is not vital that these reagents are kept distinct from the detection area as no label (fluorescent latex) is being deposited). For deposition, the cartridge is half assembled, with only the bottom and middle layer of cartridge bonded together. The reagents are pipetted into the reagent deposition zone of the half assembled test sample channel (see FIG. 26, with reagent deposition zone indicated on the cartridge as point 223, 242). These are dried in an oven at 33 deg C. for 10 min. The top layer of the cartridge is then bonded to the half assembled cartridge to produce a fully assembled three layer cartridge (see FIG. 2 for an example of how the three layers come together to form an assembled cartridge, for a different cartridge design) with dried reagents. FIG. 26 (240) indicates the shape of the double sided adhesive material which is cut away to form channels and sink structures when bonded between two layers of laminate material. The cartridge is then stored in a sealed foil pouch containing desiccant until use.

In this 2 step assay, the first binding step (functionalized latex 1 with PSA) is carried out in a wet format, before the second binding step (functionalized latex 1-PSA with functionalized paramagnetic particles) occurs using dried functionalized paramagnetic particles within the 'MST pro strip V1' cartridge as follows:

Step1

The following reagents are combined:

2 µl 0.25% functionalized latex 1 (with bound biotinylated 5A6)
6 µl 30 mg/ml BSA in PBS, pH 7.2
2 µl PSA (diluted in 60 mg/ml BSA in PBS, pH 7.2)

This first step binding reaction is incubated for 5 min at room temperature before 8 µl is added to the cartridge (as shown in FIG. 26) containing dried functionalized paramagnetic particles to fill the test sample channels. The 8 µl sample is applied to sample inlet port (226) and it fills the channels up to the fluidic stop features (229, 228, 239) 5 min binding incubation occurs before the reader brings a permanent magnet to the cartridge where it acts to collect the paramagnetic particles and anything bound to them into the detection area (222, 241). The sealing head of the reader then makes a fluid tight seal with input ports of channels 1,2,3,4,5,6 (224, 231, 232, 233, 234, 235 respectively). Whilst the paramagnetic complexes are maintained in place by the magnet, the reader carries out a wash step by expelling air from the syringe pump cartridge to displace the sample fluid from the channel, and hence remove the unbound latex from the detection area (222, 241) and displace it into the sink (236). The optical reader head then carries out a measurement of the remaining fluorescent signal (from the specific sandwich binding complexes of paramagnetic particles-PSA-fluorescent particles) which remain in air by scanning across the detection areas of each channel (222, 241) (see FIG. 24 for a description of these results).

Figure 24:
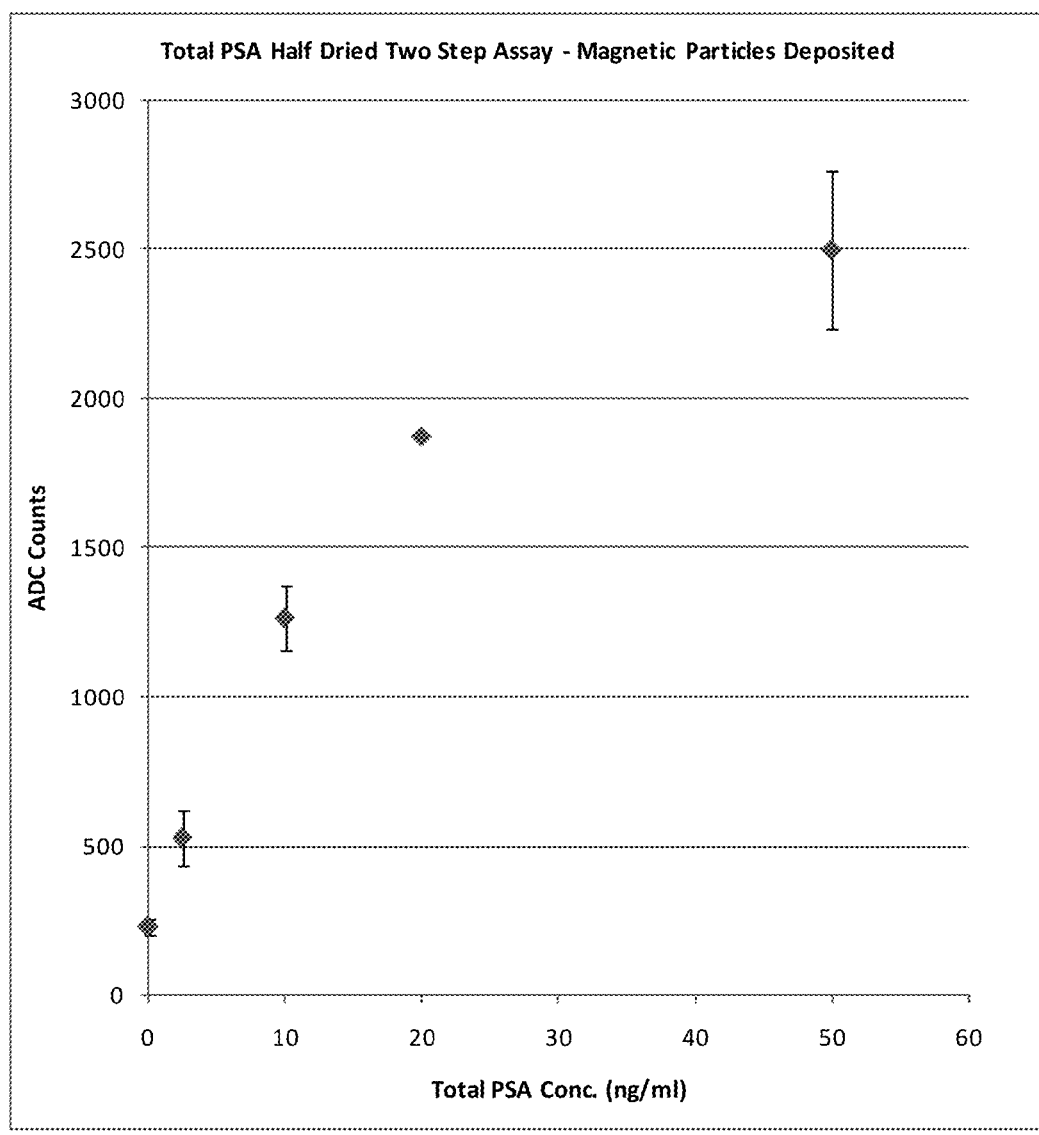
FIG. 24 shows graphed experimental results of a total PSA half dried 2 step assay performed with reagents dried in the MST Pro Strip V1 and the assay performed on the MST Pro Meter V1. In this case the magnetic particles were deposited in the test cartridge in dry format.

Results for Assay 5:

FIG. 24 shows a Total PSA two step assay performed in the MST Pro Meter and Strip, the meter using air wash step to expel unbound label from the channel. Paramagnetic particle capture phase was deposited in the strip. The meter uses an air wash step to expel unbound label from the channel. The paramagnetic particles were deposited in the strip and PSA sample/latex label was added to the strip. The meter performed an air wash and optically measured the concentration of captured fluorescent latex label. A systematic dose response curve is shown for the two step assays and demonstrate that two or three step assays can be formatted on the MST Pro Platform and that paramagnetic particles could be deposited in one strip and used to perform two step assays. These results, together with those of Assay 4 (FIG. 23) show how it would be possible to dry latex and paramagnetic particles within the same cartridge and perform a fully dry 2 step assay.

What is claimed is:

1. An assay system for conducting an assay on a fluid sample, the assay system comprising:
   (a) a microfluidic cartridge comprising
      (i) a sandwich of three layers of substrate wherein a middle layer of substrate is disposed between and adhered to a top layer of substrate and a bottom layer of substrate, the three layers of substrate together defining one or more microfluidic channels disposed therein,
      (ii) a magnetic binding agent and a fluorescently labeled binding agent disposed within said channel(s), wherein (a) the magnetic binding agent comprises a first binding moiety coupled to a magnetic or paramagnetic particle, (b) the fluorescently labeled binding agent comprises a second, different binding moiety coupled to a fluorescent label, and (c) the first binding moiety and the second binding moiety bind an analyte to be detected so that, if analyte is present, the magnetic binding agent, the analyte, and the fluorescently labeled binding agent form a complex comprising the magnetic binding agent, the analyte and the fluorescently labeled binding agent,
      (iii) a sample inlet port for introducing said fluid sample into the cartridge,
      (iv) at least one port for allowing one or more fluids to be introduced into the cartridge from an associated reader device and transported through the microfluidic channel(s) and/or for allowing air to be vented from the cartridge, and
      (v) a fluid outlet sink for removing fluid from said channel(s), wherein, prior to use in the system, the cartridge does not contain a wash liquid; and
   (b) a reader device, the reader device comprising
      (i) a receiving port for introducing the cartridge into the reader,
      (ii) a pump configured to perform an air wash to move unbound label and/or sample from a detection area in said microfluidic channel,
      (iii) a magnet or system for generating a magnetic field such that, upon application of the magnetic field or moving the magnet of the reader into close proximity with the magnetic binding agents within said microfluidic channel the magnetic binding agent is held within the detection area in said microfluidic channel by the magnetic field or the magnet during the air wash and during detection in an air environment, and
      (iv) a detector configured to facilitate fluorescent detection of, in an air environment, analyte present within the one or more of the complex(es) held in the detection area by the magnetic field or the magnet.

2. The assay system of claim 1, wherein said one or more microfluidic channels within the microfluidic assay cartridge further comprise a stop feature comprising a hydrophobic material to prevent fluid sample from passing through the microfluidic channels by capillary action alone.

3. The assay system of claim 2, wherein the stop feature is located upstream of the fluid outlet sink.

4. The assay system of claim 1, wherein the reader device further comprises an air reservoir for providing the air wash to move the unbound label and/or sample from the detection area.

5. The assay device of claim 1, wherein the pump is operative to move the fluid sample in either direction such that the fluid sample can be moved in a reciprocal motion within the cartridge.

6. The assay system of claim 1, wherein the first and/or second binding moiety is an antibody, protein, peptide or oligonucleotide.

7. The assay system of claim 6, wherein the first binding moiety is an antibody.

8. The assay system of claim 6, wherein the second binding moiety is an antibody.

9. The assay system of claim 1, wherein the detector is a fluorescence detector.

10. The assay system of claim 9, wherein the first binding moiety is an antibody.

11. The assay system of claim 10, wherein the second binding moiety is an antibody.

12. The assay system of claim 9, wherein the second binding moiety is an antibody.

* * * * *